(12) United States Patent
Leary et al.

(10) Patent No.: US 7,452,725 B2
(45) Date of Patent: Nov. 18, 2008

(54) FLOW SORTING SYSTEM AND METHODS REGARDING SAME

(75) Inventors: James F. Leary, Galveston, TX (US); Christopher J. Frederickson, Galveston, TX (US)

(73) Assignees: Board of Regents, The University of Texas System, Austin, TX (US); NeuroBioTex, Galveston, TX (US)

( * ) Notice: Subject to any disclaimer, the term of this patent is extended or adjusted under 35 U.S.C. 154(b) by 578 days.

(21) Appl. No.: 10/340,520

(22) Filed: Jan. 10, 2003

(65) Prior Publication Data

US 2003/0153085 A1    Aug. 14, 2003

Related U.S. Application Data

(60) Provisional application No. 60/347,620, filed on Jan. 10, 2002.

(51) Int. Cl.
*G01N 33/48* (2006.01)
*G01N 33/00* (2006.01)
*G01N 21/00* (2006.01)
*G01N 33/22* (2006.01)
*G01N 21/64* (2006.01)
*G01N 21/66* (2006.01)
*C12M 1/34* (2006.01)
*C12M 3/00* (2006.01)
*G01M 19/00* (2006.01)

(52) U.S. Cl. .............. 436/63; 422/58; 422/73; 422/82.05; 422/82.08; 435/288.7; 435/287.3; 73/865.8

(58) Field of Classification Search ............ 436/63; 422/73, 58, 82.05, 82.08; 435/288.7, 287.3; 73/865.8
See application file for complete search history.

(56) References Cited

U.S. PATENT DOCUMENTS

| 3,791,517 | A | 2/1974 | Freidman |
| 4,175,662 | A | 11/1979 | Zold |
| 4,756,427 | A | 7/1988 | Göhde et al. |
| 4,887,721 | A | 12/1989 | Martin et al. |
| 4,905,169 | A | 2/1990 | Buican et al. |

(Continued)

FOREIGN PATENT DOCUMENTS

DE          10031028          1/2000

(Continued)

OTHER PUBLICATIONS

Arndt-Jovin et al., "Computer-controlled multiparameter analysis and sorting of cells and Particles," *J. Histochem. Cytochem*, 1974;22: 622-625.

(Continued)

*Primary Examiner*—Jill Warden
*Assistant Examiner*—Keri A Moss
(74) *Attorney, Agent, or Firm*—Mueting, Raasch & Gebhardt, P.A.

(57) ABSTRACT

A system and method for sorting of objects that includes a pathway network that has a plurality of pathways and one or more branch points. A fluid composition including one or more objects can be transported through the pathway network, where one or more of the objects are analyzed and sorted at one or more branch points based on the analysis of the objects.

47 Claims, 13 Drawing Sheets

U.S. PATENT DOCUMENTS

| | | | |
|---|---|---|---|
| 5,100,627 | A | 3/1992 | Buican et al. |
| 5,199,576 | A | 4/1993 | Corio et al. |
| 5,204,884 | A | 4/1993 | Leary et al. |
| 5,208,651 | A | 5/1993 | Buican |
| 5,364,744 | A | 11/1994 | Buican et al. |
| 5,550,058 | A | 8/1996 | Corio et al. |
| 5,658,802 | A | 8/1997 | Hayes et al. |
| 5,736,314 | A | 4/1998 | Hayes et al. |
| 5,804,143 | A | 9/1998 | Leary et al. |
| 5,837,200 | A * | 11/1998 | Diessel et al. ............... 422/73 |
| 5,849,208 | A | 12/1998 | Hayes et al. |
| 5,858,595 | A | 1/1999 | Ziolo |
| 6,033,628 | A * | 3/2000 | Kaltenbach et al. ........ 422/68.1 |
| 6,221,654 | B1 * | 4/2001 | Quake et al. ............. 435/287.3 |
| 6,334,980 | B1 | 1/2002 | Hayes et al. |
| 2002/0005354 | A1 | 1/2002 | Spence et al. |
| 2003/0170609 | A1 | 9/2003 | Rigler |

FOREIGN PATENT DOCUMENTS

| | | |
|---|---|---|
| WO | WO 91/15750 | 10/1991 |
| WO | WO 97/30338 | 8/1997 |
| WO | WO 02/01189 | 1/2002 |
| WO | WO 03/060486 A1 | 7/2003 |

OTHER PUBLICATIONS

Chou et al., "A microfabricated device for sizing and sorting DNA molecules," *Proc. Natl. Acad. Sci. USA*, Jan. 1999;96: 11-13.

Cupp et al., "Rare Event Analysis Methods for Detection of Fetal Red Blood Cells in Maternal Blood," *Cytometry*, 1984;5: 138-144.

Duhnen et al., "A New fluidic switching sorter," *Histochemistry*, 1983; 77: 117-121.

Fu et al., "A Microfabricated Fluorescence-Activated Cell Sorter," *Nature Biotechnology*, 1999; 17: 1109-1111.

Fulwyler, M.J., "Electronic Separation of biological cells by volume," *Science*, 1965; 150: 910-911.

Fulwyler et al., "Device which seperates minute particles according to electronically sensed volume," *Rev. Sci Instruments*, 1969;40: 42-48.

Harkins et al., "Factors governing the flow cytometric analysis and sorting of large biological particles," *Cytometry*, 1987; 8: 60-70.

Hausmann et al., "Free-flow magnetophoresis: Continuous immunomagnetic sorting of cells and organelles by magnetic deviation and focusing," Cell separation methods and applications, Marcel Dekker, New York, 1998; 208-235.

Ho, C.M., "Fluidics- the Link between Micro and Nano Sciences and Technologies," *Technical Digest of the 14th IEEE International MEMS Conference*, Interlaken, Switzerland, 2001: 375-384.

Ho et al., "Micro-Electro-Mechanical-Systems and Fluid Flows," *Ann. Rev. of Fluid Mech.*, 1998;30: 579-612.

Hulett et al., "Development and application of a rapid cell sorter," *Clin. Chemistry*, 1973;19: 813-816.

Jackson et al., "Performance of in-line microfluidic mixers in laminar flow for high-throughput flow cytometry," *Biotechniques*, 2002;33: 220-226.

Jett, et al., "Droplet sorting of large particles," *Cytometry*, 1985;6: 484-486.

Kamensky et al., "Spectrophotometric cell sorter," *Science*, 1967;156: 1364-1365.

Lindmo et al., "Flow sorters for biological cells," *Flow Cytometry and Sorting*, 1990;2nd edition: 145-169.

Peters et al., "The LLNL high-speed cell sorter: Design features, operational characteristics, and biological utility," *Cytometry*, 1985;6: 290-301.

Steinkamp et al., "A new multiparameter separator for microscopic particles and biological cells," *Rev. Sci. Instruments*, 1973;44: 1301-1310.

Wallace et al., "Application of ink-jet technology to neuroscience research and biomedical research," Diller et al., *Bioprocess Engineering Symposium*, ASME Press, 1989: 153-158.

* cited by examiner

FLOW SORTING SYSTEM AND METHODS REGARDING SAME

This application claims priority from U.S. Provisional Application Ser. No. 60/347,620, filed Jan. 10, 2002, the entire content of which is incorporated herein by reference.

TECHNICAL FIELD

The present invention relates generally to sorting of objects. More particularly, the present invention preferably pertains to identification and sorting of biological materials such as cells.

BACKGROUND OF THE INVENTION

Cell sorting is necessary, or important, in many different circumstances, e.g., medical treatment, diagnostics, etc. Further, for example, an effective defense against bioterrorism demands fast, safe methods of sorting and identifying biohazardous materials. This includes infectious pathogens and pathogen-infected cells. At present, there does not appear to be a way of making existing conventional cell-sorters safe for use with pathogens and pathogen-infected cells. This is because conventional cell sorters eject droplets of cell-bearing fluids into the open air. Once the pathogens are aerosolized, containment becomes essentially impossible. Likewise, there are serious shortcomings in conventional "lab-on-a-chip" designs for cell sorting because these systems cannot operate at high enough throughput to isolate meaningful or useful quantities of sorted objects.

In addition to the safety issues, most conventional cell-sorters also utilize single sort decision cell separation technologies. In other words, conventional cell sorters are only capable of a single sort/no-sort decision. If further sort decision levels are required, the single decision level sorted cells need to be collected and reintroduced at the input of the cell sorting instrument for an additional sorting pass.

Furthermore, most conventional microfluidic cell-sorters are slow (e.g., several hundred cell per second). Even present-day, non-microfluidic, high-speed flow cytometry and droplet-based cell sorting are slow, if large (e.g., $10^8$ cells or more) numbers of cells need to be isolated. Conventional fluidic switching approaches such as those commercially available in the FACS-SortTIVI (Becton-Dickinson, Inc.), while efficient for a limited number of applications, are capable of sorting only a few hundred cells/sec and are not useful for large-scale sorting or sorting of rare cell subpopulations.

Additionally, one needs to be able to obtain live, undamaged cells suitable for further growth, testing or transplantation. This is difficult to obtain in high-speed droplet sorting due to fundamental explosive decompression and g-force deceleration problems associated with this approach. The pressure change from the flow cell side of the exit orifice to the open air occurs very quickly. This leads to the problem of explosive decompression, and can result in a cell membrane rupture, or a least cell damage, leading to decreased viability for use of such cells.

Thus, there continues to be a need for safe, sterile, high-speed, multi-parameter sorting of biological objects, such as cells, for national defense and for basic and clinical science.

SUMMARY OF THE INVENTION

The present invention provides for innovative high-speed identification, sorting, and/or purification of objects (e.g., biological objects) that addresses the problems associated with traditional sorting techniques. The present invention allows for multi-step sorting with re-sorting decisions done in an integrated sequence as the objects are sorted and re-sorted at different levels of the multi-stage and/or multi-branched device.

The flow sorting method of the present invention can include one or more of the following features: providing a pathway network that includes a plurality of pathways and one or more branch points; transporting a fluid composition comprising a plurality of objects (e.g., cells suspended in a fluid composition) through the pathway network; analyzing one or more of the objects in the pathway network; sorting cells at the one or more branch points based on the analysis of the cells; and/or directing at least one of a plurality of objects (e.g., particles, cells) through the one or more branch points based on the analysis of the objects. The objects directed according to the sorting method can include: biological objects, such as cells and/or non-biological objects, such as particles (e.g., beads). Other objects can be separated according to the present invention as well.

The present invention, such as the transporting of the fluid composition, can also include one or more of the following features: a plurality of pathways and one or more branch points that provide for a progressively greater number of pathways; repeatedly separating a fluid composition into progressively greater numbers of pathways; adjusting a flow rate of a fluid composition through one or more pathways during analysis of objects; stopping a fluid composition in one or more of the plurality of pathways during analysis of objects; and transporting a fluid composition through a plurality of pathways in a fluid tight system. Analyzing one or more of objects (e.g., cells, particles, etc.) according to the present invention can include one or more of the following features: analyzing objects during a particular period of time using each of the sorting modules of at least one sorting stage for use in directing the one or more objects through associated branch points; analyzing objects at multiple sorting stages; performing at least one of morphology measurements, luminescence measurements, fluorescence measurements, radioactive measurements, light scattering measurements, electrical measurements, or ultrasound measurements for use in determining one or more characteristics of one or more of the objects; providing electromagnetic energy to one or more objects; detecting electromagnetic energy returned from one or more objects resulting in a measurement signal; providing one or more characteristics of at least one object based on the measurement signal; and taking two or more different measurements from the objects being analyzed; using prior analysis and directions of the objects in directing one or more of the objects through subsequent branch points.

The methods according to the present invention can also include one or more of the following features: combining a plurality of objects directed through each of two or more branch points prior to directing the combined objects through a subsequent branch point; directing a plurality of objects through a branch point prior to directing at least one object of the plurality of objects through a subsequent branch point; applying a magnetic field to direct the fluid composition based on the analysis of the objects; operating a flow switching structure associated with a branch point based on the analysis of the objects; providing makeup fluid into one or more of the plurality of pathways (e.g., changing at least one of a proportion of the makeup fluid and the fluid composition through one or more of the plurality of pathways); one or more branch points that form a series of pathways, where directing at least one of the plurality of objects includes sorting one or more objects by directing the objects down the series of pathways by repeatedly analyzing and directing one or more of the objects through multiple branch points based on the analysis of the objects; one or more branch points that form at least a portion of one or more sorting stages, where each sorting stage comprises at least one sorting module associated with each of a plurality of branch points; using at least one of one or more branch points to provide parallel pathways from a single combined pathway, where the single combined pathway is provided by pathways from a plurality of branch points; sorting one or more objects in the single combined pathway by directing the objects through the at least one of the one or more branch points to one or more of the parallel pathways; using at least one of the one or more branch points to provide parallel pathways from a single pathway, wherein the single pathway is provided by a pathway from a single branch point; and sorting one or more objects by directing the objects through the at least one of the one or more branch points to one or more of the parallel pathways.

A sorting system (e.g., a cell sorting system) of the present invention can include one or more of the following features: a pathway network comprising a plurality of pathways operable to receive a fluid composition comprising a plurality of objects, where the pathway network further comprises one or more branch points; one or more analyzer devices at one or more positions of the pathways for use in analyzing one or more of the plurality of objects that flow in the pathways; one or more fluid flow controllers, where at least one fluid flow controller associated with at least one of the one or more branch points is operable to direct at least one of the objects (e.g., cells) in the plurality of pathways based on analysis of the objects; a control apparatus; a control apparatus operable to receive a measurement signal from at least one analyzer device and determine at least one characteristic of an object based on the measurement signal; a control apparatus operable to provide a control signal to a fluid flow controller based on the at least one characteristic of the object.

The pathway network of the present invention can include one or more of the following features: at least one of one or more branch points being used to provide parallel pathways from a single combined pathway, where the single combined pathway is provided by pathways from a plurality of branch points; at least one of the one or more branch points being used to provide parallel pathways from a single pathway, where the single pathway is provided by a pathway from a single branch point; the pathway network includes a single pathway separated into two or more additional pathways by at least one of the one or more branch points; and a series of pathways, each branch point from the series of pathways having at least one analyzer device and at least one fluid flow controller associated therewith to allow for a sequential analysis and sorting of objects through a progression of branch points.

The sorting system (e.g., a cell sorting system), can further include one or more of the following features: each of a plurality of branch points can have at least one analyzer device and at least one fluid flow controller associated therewith to allow for a parallel analysis and sorting of objects simultaneously; at least one analyzer device and at least one fluid flow controller that are associated to form a sorting module associated with each of a plurality of one or more branch points, where at least one group of the sorting modules is arranged and operable for parallel analysis and sorting of objects, where each group of sorting modules forms a sort stage; two or more sort stages.

The one or more analyzer devices of the present invention can also include one or more of the following features: analyzer devices operable for use in analyzing biological objects that flow in the pathways (e.g., the biological objects can include cells); one or more analyzer devices operable for use in analyzing the cells that flow in the pathways; one or more analyzer devices operable for use in analyzing non-biological objects that flow in the pathways, where the non-biological objects can include particle (e.g., beads); one or more analyzer devices positioned at or before one or more branch points; one or more analyzer devices operable to perform at least one of optical measurements, luminescence measurements, fluorescence measurements, light scattering measurements, radioactive measurements, electrical measurements, and ultrasound measurements; at least one exciter; at least one exciter tuned at a specific wavelength to cause fluorescent markers to fluoresce; and at least one detector (e.g., a charge-coupled device (CCD) detector).

The one or more fluid flow controllers of the present invention can also include one or more of the following features: being operable to stop the one or more objects in a pathway; operable to adjust a flow rate of the objects in the plurality of pathways; a flow switching structure operable to direct fluid composition in the pathways; at least one of a mechanical multi-way valve, a rotary valve, a magnetic solenoid shuttle valve, and an elastomeric valve.

The system can also further include one or more of the following additional features: a fluid manifold containing fluid and one or more makeup fluid ports; one or more makeup fluid ports connecting a fluid manifold and the pathways to allow for fluid to be provided to one or more of the pathways of the sorting system from the fluid manifold; at least one branch point operable to receive fluid composition from multiple branch points via multiple pathways and provide fluid composition to one or more pathways; at least one branch point operable to receive fluid composition from a single branch point via a single pathway and provide fluid composition to one or more pathways; each of a plurality of one or more branch points and at least portions of associated pathways being provided as a separate branch point module; a separate branch point module configured to be assembled for use as at least a portion of a pathway network; two or more separate branch point modules configured to be assembled for use as at least a portion of the pathway network; each of two or more separate branch point modules configured with at least a portion of a different analyzer device; each of two or more branch point modules configured to be inserted into a holding frame for use as at least a portion of a pathway network; at least one of two or more separate branch point modules having a different flow path configuration than another of the plurality of branch point modules; at least one of two or more separate branch point modules is operable, when assembled, to receive fluid composition from multiple branch points via multiple pathways and provide fluid composition to one or more pathways; and at least one of the two or more separate branch point modules is operable, when assembled, to receive fluid composition from a single branch point via a single pathway and provide fluid composition to one or more pathways.

DETAILED DESCRIPTION

Figure 1A:
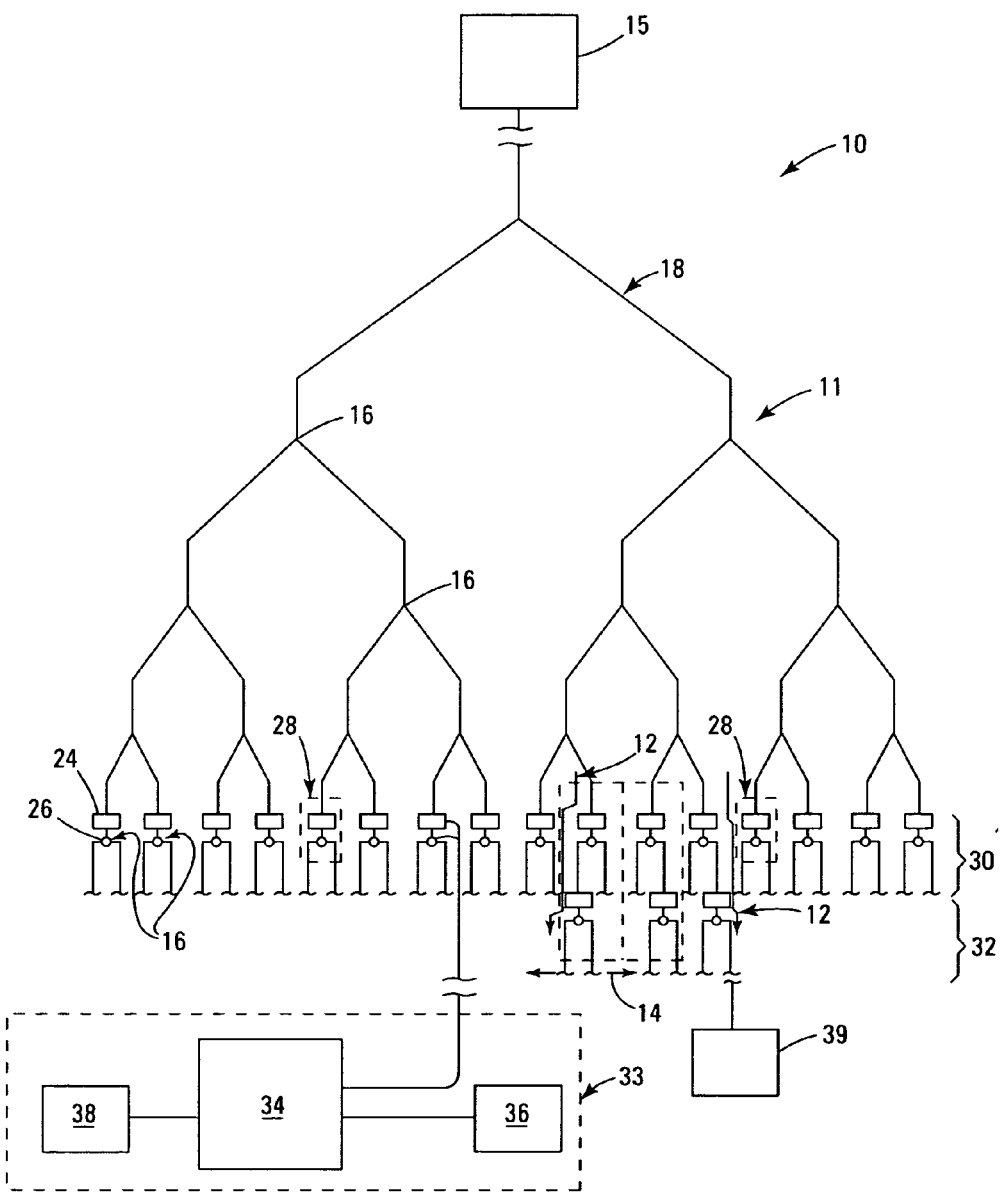
FIG. 1A shows a schematic of a multiple pathway object sorting system according to one embodiment of the present invention.

In the following detailed description of the embodiments, reference is made to drawings that form a part hereof, and in which are shown by way of illustration, specific embodiments in which the invention may be practiced. It is to be understood that other embodiments may be utilized and processing step/structural changes may be made without departing from the scope of the present invention.

The present invention described herein may be used in various types of research, such as in pharmaceutical, biotechnology, medical device industries, and also used by researchers involved in stem cell research, cancer research, infectious disease research, and/or preparation of cells (e.g., isolation of desired cells with purging of undesired cells) to be used in transplantation, drug discovery and development utilizing gene expression measurements. In addition, bead-based assays for many molecules can be used for the high-throughput screening of libraries of sequences of nucleic acids or peptides for drug discovery or for basic or clinical research.

The following description includes various features of the present invention, where one or more of such features may be used separately or in combination according to the present invention. Generally, the present invention provides a system and/or a method for sorting of objects, including non-biological objects and, preferably, biological objects such as cells. In addition, the objects can include, but not limited to, compound objects. For example, compound objects can include cells attached to beads or cells attached to each other, and in other readily conceivable combinations of multiple biological or non-biological objects. The sorting of the objects according to the present invention also allows for the enrichment of objects of interest and for the improvement in viability of the separated biological objects due to the processing conditions used in the present invention.

More specifically, the present invention includes a system and/or method for sorting objects in a fluid composition. As used herein, the term sorting can include any process according to the present invention that separates and/or isolates objects based on measurements taken from the objects. In conducting the sorting, the objects in the fluid composition are thereby enriched, where the term enriched, or enriching, includes any process according to the present invention that increases the concentration of separated objects. Thus, sorting of the objects can lead to their enrichment. Hereinafter, the term sorting will be used, but it is understood that in the act of sorting there is enrichment of the objects.

As used herein, the term viability as used with the separated biological objects includes sorting of biological objects under conditions that maintain and/or enhance the separated biological objects capability to live and/or grow once sorted according to the present invention or to be usable for subsequent processes such as gene expression or protonic analyses by other processes.

As used herein, a fluid composition can include any combination of solutes and/or solvents necessary for suspending and/or maintaining the viability, integrity and/or chemical stability of the objects. For example, the fluid composition can include biological growth media formulated to maintain and support the growth and viability of biological objects, such as cells. Preferably, the fluid composition includes one or more of the following: salts, serum, buffers, and any other components needed to maintain the viability and stability of living cells.

Generally, the present invention for sorting the objects includes a pathway network operable to receive and transport the fluid composition that includes a plurality of objects (e.g., cells) through the pathways. Preferably, the pathway network includes a plurality of pathways and one or more branch points. At each of the branch points, for example, the pathways can separate into two or more additional pathways.

The present invention can further include one or more analyzer devices at one or more positions along the pathways. Preferably, the one or more analyzer devices are operable to analyze the objects that flow in the pathways. The present invention can also include one or more fluid flow controllers. The one or more fluid flow controllers are operable to direct at least one of the plurality of objects through the one or more branch points based on the analysis of the objects.

The pathway network of the present invention can allow for the fluid composition being transported therein to be repeatedly separated into progressively greater numbers of pathways. Alternatively, the pathway network can allow for objects in the fluid composition being transported therein to be directed through one or more branch points, where these directed objects are subsequently combined prior to directing the combined objects through a subsequent branch point. In other words, objects having been directed from two or more branch points can be combined with each other prior to entering a subsequent branch point.

Preferably, using the fluid flow controllers and the analyzer devices of the present invention, there can be sequential and parallel identification and sorting of objects as they move along the pathways and through the branch points. For example, in sequential identification and sorting, a plurality of objects can be directed through a branch point of the one or more branch points prior to directing at least one object of the plurality of objects through a subsequent branch point. In other words, a sequential series of branch points can be used in directing the objects, where a branch point can be used to direct a plurality of objects before directing at least one of those objects through a subsequent branch point. The concept of series "stages" and parallel identification and sorting will be discussed in detail herein.

In one or more embodiments, the pathways may include closed channels, flow channels, tubes, conduits, or micro-channels. These terms may be interchanged and/or substituted with each other. However, such pathways do not necessarily need to be closed conduits, but such closed conduits provide benefits associated with sorting hazardous objects.

As used in this document, the use of the term "object" includes, but is not limited to, biological material, such as microorganisms. For example, the microorganisms can include, but are not limited to cells, which can include prokaryotic or eukaryotic cells, and can include without limitation, bacteria, protozoa, fungal cells, invertebrate cells such as insect cells, and vertebrate cells such as mammalian cells, including human cells or even parts of those cells such as sub-cellular organelles (e.g., mitochondria). Other cell types of industrial or clinical significance can be used with the present invention.

Alternatively, biological material, and objects that include specific examples of these biological materials, can include but is not limited to DNA, RNA or proteins, chromosomes, prions, viruses, parasites, bacteria, and other micro-organisms and other discrete biological and non-biological objects as designed for and applied to the problem of screening large numbers of live cells, e.g., selection and isolation of pluripotent stem cells from blood, interstitial fluids, or any other bodily tissue homogenate, suspension, or fluid.

The system and method of the present invention can also be used in analysis and sorting of non-living objects, such as beads, that permit examination of molecules. Examples include, but are not limited to, bead-based chemistries that can allow for measurement of specific molecules in the absence of cells. Alternatively, the present invention can be used in combinatorial chemistry for use in generating libraries for applications such as drug development. In addition, the sorting abilities provided by the present invention can permit combinatorial chemistry to be performed. For example, the system and/or method of the present invention can be applied to the problem of identifying, sorting and/or collecting individual peptides, proteins, DNA, RNA or other molecules, e.g., in bead-based or combinatorial chemistries.

FIG. 1A shows one embodiment of a multiple pathway sorting system 10 according to the present invention. The multiple pathway sorting system 10 provides for a pathway network 11 that includes multiple pathways 18 that branch out from branch points 16 into, in this example, progressively greater numbers of pathways 18. To accomplish this, single pathways in the pathway network 11 can separate into two or more additional pathways 18 at the one or more branch points 16. In the present example, the pathways 18 branch out to provide for a multiplicity of parallel processing pathways for the objects moving through the multiple pathway sorting system 10.

The multiple pathway sorting system 10 of FIG. 1A displays both a serial architecture, represented by arrow 12, and a parallel architecture, represented by arrow 14. As used herein serial architecture refers to the sequential sorting of objects through the use of a progression of sorting modules (e.g., a combination of analysis device and fluid flow controller as will be discussed herein) in multiple sort stages. As used herein parallel architecture refers to the parallel sorting of objects simultaneously (e.g., analysis and sorting at two sorting modules across the same level of the pathway network 11), such as across a single stage of modules.

The dividing of the fluid composition into multiple sort stages leads to a throughput capability that is essentially exponential. While the parallel paths scale essentially according to the relative number of paths or n-furcations at each branch point, the sequential staging can scale far larger because of the ability to divert fluid composition containing unwanted objects down other pathways and thereby effectively concentrate the number of desired objects per unit of fluid volume. This allows for gradual examination of potentially multiple objects in a bolus of examined fluid in early stages and a gradual process of refinement to allow single desired object measurements at the later sorting stages. Hence, unlike other object sorting devices, the initial measurements may be taken on multiple, rather than single objects. All of this leads to tremendous increases in total throughput of objects and increases in yield and purity of desired objects not possible by conventional flow cytometry or lab-on-a-chip instrumentation.

FIG. 1A also provides a fluid composition source 15. Generally, the fluid composition source 15 contains the fluid composition having the to-be-sorted population of objects. The fluid composition source 15 can include one or more fluid tight containers for holding the fluid composition. The fluid composition source 15 can also include one or more inlet ports to allow for introduction of the fluid composition into the container of the fluid composition source 15.

The fluid composition source 15 can also include one or more mechanisms for developing a pressure head in the fluid composition to allow for the fluid composition to be moved through the pathway network 11. Examples of such mechanisms include, but are not limited to, pumps that can include positive displacement pumps such as peristaltic pumps or syringe pumps. Other types of pumps or mechanisms are also possible for developing the necessary pressure to move the fluid composition through the pathway network.

In FIG. 1A, the to-be-sorted population of objects are randomly received from the fluid composition source 15 and separated into multiple parallel pathways 18. This spreading out of the fluid into multiple parallel pathways does not require active fluid sorting. It is merely a way of parallel processing the fluid composition into a number of different sorting modules (discussed herein) positioned in the pathway network 11. The benefits of such a parallel processing and division of the sorting into distinct stages are enormous in terms of overall processing speeds.

The present invention also offers advantages with respect to the operating pressure of the fluid composition moving through the multiple pathway sorting system 10. In one example, one or more pressurized fluid sources (e.g., fluid pumps) can be used to add additional fluid ("makeup" fluid, as will be discussed herein) through the multiple pathway sorting system 10. This aspect of the present invention gets around the "pressure head" problem of requiring more and more pressure to drive the fluid composition down smaller and smaller pathways.

If the appropriate amount of fluid is added, the downstream pathways do not need to have reduced diameters (or areas), since more fluid can be added to compensate for the additional volume as new pathways, perhaps at the same cross-sectional area, are added. In addition to providing additional fluid as needed, the "makeup fluid" can also be functional in that it can contain different fluid components that may affect the objects in some way. The effect produced by the makeup fluid on an object at some stage can then be measured at a subsequent stage. This allows for objects to be changed by the effects of the fluid as they progress through the overall system.

One distinct advantage of the multiple pathway sorting system 10 is that the number of pathways 18 used in separating the objects can be increased without the need to increase the pressure used to drive the fluid composition carrying the objects. This is because two pathways can carry twice the number of objects (volume of fluid) at the same driving pressure needed for one, and four pathways can carry four-fold the fluid at the same pressure and so on. By adding the makeup fluid, the entire system can be maintained at a single pressure, if desired, and can avoids any pressure drops which could decrease viability of living cells or stability of other objects.

In addition, since there is no requirement in the present invention for immediate decompression of sorted objects in the fluid composition, the viability problems of explosive decompression of live cells in droplet sorters are circumvented. For example, in one embodiment, the objects in the fluid composition can be sorted at very high pressures and then brought slowly back to atmospheric or lower pressures after sorting. This then allows for successive stages (e.g., parallel groups of sorting modules, as will be discussed herein) to have smaller diameter cross-sections. Since the sorted volume can be transported or delivered down smaller cross section pathways, if desired, the distance between sorted objects is increased. As such, a given switching time to exclude more volume (and unwanted surrounding objects) is possible, allowing greater sort purity at each stage.

Another advantage of the design is that the serial-parallel architecture allows full Boolean logic to be used in the sorting of objects. A cell, for example, with a certain fluorescent tag can be selected "on" at one sorting stage, then if carrying a second marker can be selected "on" at the next sorting stage, and so on, according to multiple characteristics measured from those objects. Additionally, branching tree or recursive partitioning classification (e.g., both in terms of sort decision trees using methods such as Classification and Regression Tree (CART) statistical decision trees and in terms of actual physical sorting) methods can be employed so that much more sophisticated sorting decisions can be employed. The branching tree fluidic architecture of the present invention lends itself well to these modern and sophisticated statistical methods such as CART analysis or to other methods such as neural network analyses.

Referring again to FIG. 1A, the branch points 16 of the pathway network 11 can be arranged in a wide variety of series and parallel architectures 12 and 14. Essentially, the branching of the pathway network 11 can be designed with as many branch points 16 in as many designs of series and parallel architectures 12 and 14 as desired. The series and parallel architectures 12 and 14 of the pathway network 11 allow for the fluid composition that include the objects to be repeatedly separated into a progressively greater number of pathways 18, ending, for example, in a plurality of parallel pathways. The fluid-flow architectures of the present invention can be constructed in massive array structures in which the particular fluid flow architecture can be easily reconfigured by software or other methods to close or inactivated undesired regions of this parallel fluidic processing array. Further, the array can be assembled in modular fluidic building blocks as desired, as discussed herein.

As shown in FIG. 1A, the branch points 16 bifurcate the pathways 18. However, it is understood that as described herein, the branch points 16 can include not only bifurcations, but also h-furcations, wherein "n" is any positive integer greater than 2 (e.g., multiple pathways 18 emanating from a single pathway). In addition, each branch point 16 of the present invention can include pathways 18 having any number and/or combination of pathways 18 emanating from the branch points 16 (e.g., each branch point can have a different number of n-furcations). In other words, the pathways 18 and the branch points 16 can be used to form pathway network 11 that is non-uniform.

Figure 2:
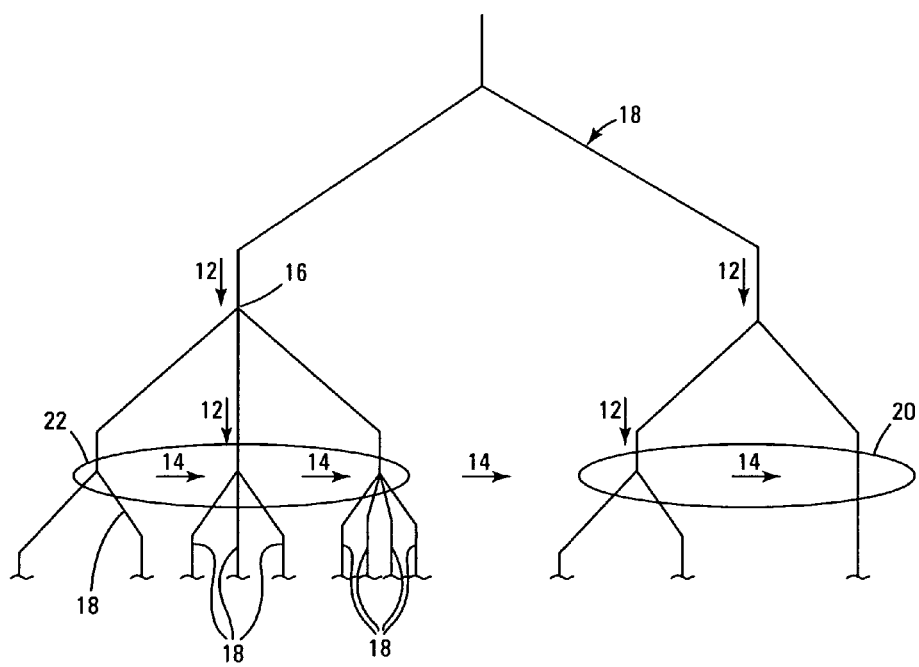
FIG. 2 shows a schematic of an additional embodiment of a pathway apparatus that may form a part of the sorting system shown in FIG. 1A-C.

By way of example, FIG. 2 shows one example of a portion of a pathway network 11 that is non-uniform. As FIG. 2 shows, branch points 16 across the parallel architecture 14 could have the same number of pathways 18 emanating from the branch point (shown generally at 20), or a different number of pathways 18 emanating from each branch point as compared to other branch points 16 across the parallel architecture 14 of branch points 16 (shown generally at 22). As a result, this architecture permits multi-way rather than two-way sorting of objects at a given branch point. Similarly, each branch point along the series architecture 12 of branch points 16 could have the same number of pathways emanating from the branch point, or a different number of pathways emanating from the branch point as compared to the other branch points 16 along the series architecture 12 of branch points 16. In addition, the lengths of the pathways 18 in the pathway network 11 can be similar or can vary depending upon the uniformity or non-uniformity of the pathway network 11.

Referring again to FIG. 1A, the multiple pathway sorting system 10 further includes analyzer devices 24 at one or more positions along the pathways 18. As shown in FIG. 1, the analyzer devices 24 can be, for example, positioned at or before a branch point 16 of the pathway 18.

Generally, the analyzer device 24 can include any analyzer device capable of detecting characteristics and making measurements of the characteristics from objects. The analyzer devices 24 are each operable to take measurements on objects moving through the pathway 18 and to analyze the objects therein. Various types of measurements can be taken with respect to the objects to provide information concerning the same as is discussed more fully herein.

The pathway network 11 also includes fluid flow controllers 26. The fluid flow controllers 26 are operable to direct flow of the fluid composition in the pathways 18, for example, based on analysis of the objects that flow in the pathway 18. Generally, the fluid flow controller 26 can include any controller device capable of directing fluid flow through one or more of the pathways based on one or more received control signals.

As shown in FIG. 1A, the fluid flow controllers 26 can be located at, or just prior to, the branch point 16 or any other location for suitably directing the fluid. Preferably, each fluid flow controller 26 operates to direct the flow of the fluid composition, including the object, through a branch point 16. In one embodiment, each fluid flow controller 26 can be activated (e.g., controlled) by, directly or indirectly, an analyzer device 24 that is associated with the same branch point 16. Alternatively, the decision to activate a fluid flow controller can be based not only on the analyzer device 24 that is associated with the same branch point 16, but on multiple inputs from analyzer devices 24 occurring upstream in the system 10.

The fluid flow controller 26 and the analyzer device 24 at a given branch point 16 can operate together for use in sorting objects that will be delivered to a subsequent branch point 16. To this end, the fluid flow controller 26 and the analyzer device 24 at a given branch point 16 can be viewed, and referred to, as a sorting module 28. It will be recognized that each sorting module 28 may include one or more fluid flow controller 26 and/or analyzer device 24. In addition, sorting modules 28 having different combinations of analyzer devices 24 and/or fluid flow controllers 26 can be used in any combination either across the parallel architecture 14 and/or down the series architecture 12 of the system 10.

As will be noted in FIG. 1A, the pathway network 11 allows the fluid composition to spread out into multiple parallel pathways 18 (e.g., the number of pathways 18 can at least double at each branch point 16). This initial spreading out of the fluid composition does not necessarily require the use of active fluid sorting (e.g., use of the sorting module 28) at the early branch points 16 of the sorting system 10. So, when active fluid sorting is not used at these early branch points 16, the pathway network 11 provides a way of separating the fluid composition into a number of different pathways 18 leading to sorting modules 28.

In one embodiment, groups of sorting modules 28 arranged across the parallel architecture 14 of the system 10 can be referred to as a sorting stage 30. Multiple sorting stages can be used in the multiple pathway sorting system 10. For example, a second-sort stage 32 can be used after sort stage 30 to allow for a further sorting of the objects based on one or more additional measurements taken at the sorting modules of the second-sort stage 32.

Figure 3:
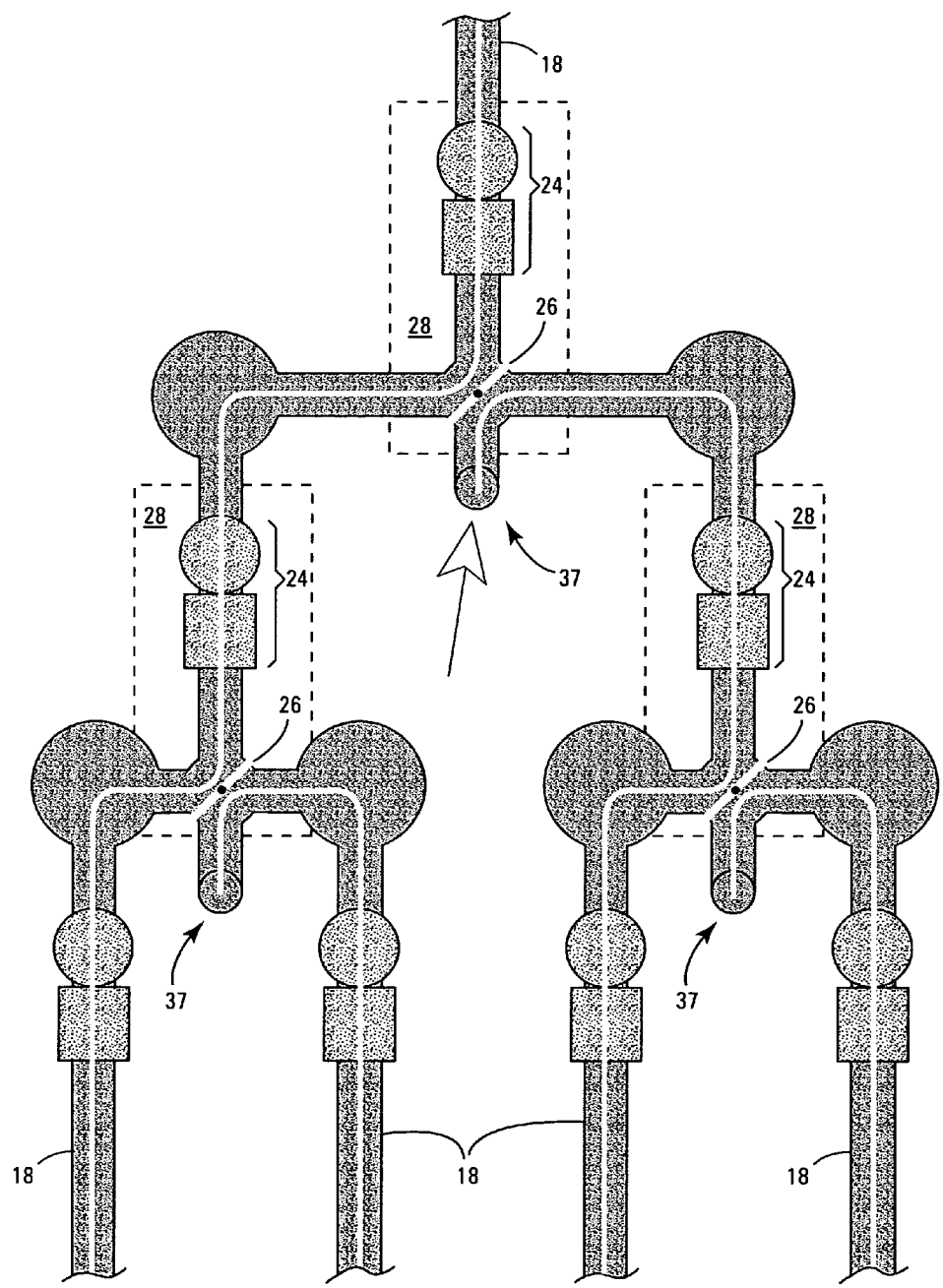
FIG. 3 shows a schematic of another embodiment of a pathway apparatus that may form a part of the sorting system shown in FIG. 1A-C.

FIG. 3 shows one example of a portion of a multiple pathway sorting system 10. The portion of the multiple pathway sorting system 10 in FIG. 3 includes pathways 18 and sorting modules 28. In addition, the multiple pathway sorting system 10 can further include a makeup fluid port 37. The makeup fluid port 37 allows for additional (i.e., "makeup") fluid to be provided to the sorting system 10 downstream of a closed fluid flow controller 26 (e.g., a rotary valve, as will be discussed herein).

Providing the additional makeup fluid helps to maintain the flow velocity, flow volume and pressure on the downstream side of a closed fluid flow controller 26. In other words, the additional fluid entering the sorting system at the sorting modules 28 helps to maintain flow velocity, flow volume and pressure through out the entire sorting system 10. Introduction of the makeup fluid into the pathways 18 can also have a diluting effect on the objects. In other words, by adding the makeup fluid, the proportion of the makeup fluid and the fluid composition changes in the pathways during the analysis of the objects. As such, the makeup fluid can also be referred to as a diluent. Preferably, the additional fluid, for example, is a plain fluid composition (i.e., fluid composition without objects) used to move the objects in the sorting system 10. As described herein, the makeup fluid can also introduce additional molecules or components and can be used to affect the objects. The effects of that new makeup fluid exposure can be measured in subsequent stages, leading to more complex and dynamic experimental conditions.

In one example, the additional fluid is introduced into the makeup fluid port 37 from a fluid manifold. Preferably, the fluid manifold can be positioned beneath the pathway network 11. The pressure of the makeup fluid in the fluid manifold can be maintained at or above the pressure of the fluid composition in the sorting system 10 to ensure that fluid composition from the pathway network 11 does not flow back into the fluid manifold. In one embodiment, a positive pressure of makeup fluid relative to the fluid composition in the system 10 will allow for the makeup fluid to ensure that there is fluid to keep the pressure in the pathways consistent in the embodiment where the pathways do not narrow down in successive stages to allow for conservation of the original fluid volume. Adding makeup fluid in this manner helps circumvent the problem of increasing the pressure that would be required to drive the objects and fluid down smaller and smaller pathways at each stage.

Generally, each analyzer device 24 can provide one or more measurements characterizing an object in the pathway 18. The analyzer device 24 can be used to take any number of characteristic measurements from the objects in any number of manners using a wide variety of hardware and software devices. In other words, a wide variety of devices, e.g., hardware and software, may be used to implement the analyzer devices 24 to provide one or more various types of characteristic measurements.

Characteristics of the objects can include, but are not limited to, any number of qualities or properties that can be measured from the object (e.g., physical, chemical, electrical such as impedance or resistance signaling, magnetic, ultrasound, etc.). For example, physical characteristics measured from the objects can include the size, the shape, surface charge, resistance (similar to Coulter counter) and/or the morphology of the object. Characteristics of luminescence and/or fluorescence can also be measured from objects having been marked with specific compounds having these characteristics. Since it is possible to alter the velocity of objects at different stages, a much wider range of fluorescence lifetimes, including if slowed enough, luminescence can be possible that was not possible on conventional flow cytometric sorting systems.

Hardware that can be used for taking measurements includes, but is not limited to, hardware for performing optical, luminescence, fluorescence, and/or non-optical methods such as electrical impedance, magnetic properties, radioactive, besides others. Examples of optical measurements include, but are not limited to, light scattering measurements, and optical measurements of object size and/or morphology. In addition, examples of luminescence and fluorescence measurements include, but are not limited to, measurements taken on objects stained with or marked with one or more biologically specific marker such as fluorescent antibodies, fluorescent protein stains, tagged nucleic acid or peptide sequences, etc.

With relatively "hot" radioactive probes, appropriate flow rates combined with appropriate radioactivity detectors may allow measurements of the amount of radioactivity (one or more radioisotopes) per object. With a closed pathway architecture, this is another example where radioactive probes could be used safely as opposed to presenting a hazard in aerosol-based sorting systems. By combining radioactive atom capture mechanisms on objects such as beads, and stop-flow capability, very minute amounts of radioactive material could be detected. Again, the ability to control flow rates and to have disposable (and more shieldable) sorting architectures provides for useful applications of this invention.

Examples of radioactive measurements include, but are not limited to, measurements for specific radioisotope labeled cells (e.g., cells labeled with $P^{32}$, $I^{125}$, $C^{14}$, or other radioisotopes in one or more forms that can taken up by cells). More specific examples of this aspect of the present invention will be discussed herein.

In an exemplary embodiment, the objects can be marked or labeled with two or more fluorescent markers that fluoresce as different wavelengths, where each marker can be specific for different structures in and/or on the object. In this example, the analyzer device 24 can include two or more exciters (e.g., light sources) that are each specifically tuned to specific wavelengths that cause each of the two or more fluorescent markers to fluoresce. Further in the exemplary embodiment, a detector in the analyzer device 24 (as will be discussed more fully herein) can be used to sense fluorescence from the objects as it occurs.

In addition to making measurements using fluorescent markers, the analyzer device 24 can also take additional measurements from the objects. For example, measurements of object size, object shape, object configuration (e.g., clusters of objects) can be obtained. Any number of measurements may be used in combination to assist in the sorting of objects (e.g., cells) according to the present invention.

As will be appreciated, the analyzer devices 24 require time to take the measurements on the objects. As such, it may be required to adjust the flow rate of the transportation of the fluid composition through one or more pathways during analysis of the objects. Adjusting the flow rate of the transportation of the fluid composition through one or more pathways during analysis can include stopping the fluid composition to allow for measurements to be taken on the objects by the analyzer devices 24. In one embodiment, adjusting the flow rate may be accomplished by using fluid flow controllers 26. For example, a fluid flow controller 26 can be used to adjust the flow rate of the fluid composition, including stopping the flow, in one or more branches of the pathway 18 in which a particular analyzer device 24 is located. Using the fluid flow controller 26 to adjust the flow rate of the fluid composition can allow sufficient time for measurements to be taken on the objects. In addition, the objects can undergo further manipulations (e.g., microinjection or treatment of the cells or objects with other agents or reagents) while stopped by the fluid flow controller 26 before "releasing" the objects for further measurements or sorting, either through makeup fluid of different composition at that point or the introduction of agents from another attached device.

The fluid flow controllers 26 can include one or more of a variety of devices to direct fluid composition in the pathways 18 based on analysis of the objects (e.g., based on measurements by an associated analysis device 24). For example, the fluid flow controllers 26 can include a flow switching structure such as, for example, a valve structure and associated hardware. Examples of the valve structure include, but are not limited to, mechanical multi-way valves such as two-way valves, three-way valves, rotary valves, a magnetic valves such as magnetic solenoid shuttle valves, pneumatic valves, a hydraulic valves, and/or electrical valves. In one example, the valve structure can be integrated into the pathways 18, for example, at or adjacent the branch points 16.

The fluid flow controllers 26 can, alternatively, include use of an electrostatic field, an electromagnetic force and/or the other techniques to direct fluid flow. In one embodiment, an electromagnetic force, influences the ferrofluid and object flow as described herein, thereby performing magnetic sorting at the single-object level as opposed to bulk magnetic sorting as performed by conventional technologies. This represents an example of electromagnetic rather than mechanical sorting.

With further reference to FIG. 1A, the example of sorting system 10 of the present invention further includes a control apparatus 33 for use in controlling one or more components of the system 10 (e.g., analyzer devices 24, fluid flow controllers 26, etc.). For example, the analyzer device 24 can provide one or more signals related to characteristics of the measured objects to the control apparatus 33. The control apparatus 33 can then determine at least one characteristic of the object based on these signals. The control apparatus 33 can then provide a control signal to the fluid flow controller 26 for directing the flow of the fluid composition based on at least one characteristic of the analyzed object.

Any number of devices could be used as the control apparatus 33 for the present invention. Preferably, the control apparatus 33 includes a computer system 34. The computer system 34 can include one or more data input/output structures operatively coupled to one or more of the analyzer devices 24 and a corresponding fluid flow controller 26. Further, for example, the control apparatus 33 can further include signal conditioning electronics to perform, if desired, analog to digital conversion, filter and/or amplify the signals from the analyzer devices 24 to be provided to the computer system 34 (e.g., measurement data) and provide signals for controlling the operation of the analyzer devices 24 and/or the fluid flow controllers 26 in real-time. Preferably, the computer system 34 of the controller apparatus 33 can be used in performing and/or assisting in performing data analysis on the measurements taken by the analyzer devices 24.

The computer system 34 can also include, besides other things, memory for storing one or more programs and/or for use in executing and/or assisting in performing the data analysis on measurements received by the computer system 34. Such programs can be executed on one or more microprocessors of the computer system 34. The computer 34 can also be used to store the measurement data of sorted and/or unsorted cells and to choose sort windows and appropriate Boolean combinations of windows to produce overall sorting protocols. The computer system 34 can further include a monitor 36 for viewing the operational status of the sorting system 10. The computer system 34 can also further include a keyboard 38, or any other type of input tool, for providing instructions to the computer system 34.

The control apparatus 33 further may include various types of analysis and control software. For example, control and data analysis software allow for one or more cell subpopulations to be sorted simultaneously. For example, a CART (Classification and Regression Tree) analysis can be used, wherein the CART is a useful approach for the present invention as it provides a multivariate statistical decision boundary at each branching node. Use of modern digital signal processing electronics allows, for example, complex mathematical classification algorithms to be performed in real-time for very sophisticated sort decisions.

In an additional example, the control and data analysis software can include LabVIEW software (National Instruments Corporation, Austin Tex.) for use in controlling the sorting system 10, and/or providing data analysis of the received signals. It will be recognized that various types of software may be used to provide analysis of measurements provided by the analyzer devices 24, provide control of the fluid flow controllers 26, provide a user with one or more graphical user interfaces for use in controlling the sorting system 10, provide for visualization of the operation of the sorting system 10, or provide any other functionality required for operation of the sorting system 10.

An additional beneficial feature of the sorting system 10 of the present invention is that the objects being sorted can be maintained under controlled conditions (e.g., controlled pressure conditions) to prevent explosive decompression problems as the objects emerge from the system 10. In addition, the objects being sorted with the sorting system 10 of the present invention can, in one or more embodiments, be completely contained, thereby reducing the likelihood of contaminating the environment in which the system 10 of the present invention is being operated. The closed fluidic architecture of at least one embodiment of the present invention also permits the analysis of objects in the absence of gravity, thus making it possible to perform analysis and sorting of cells and objects in ultra-low gravity regimes such as in space.

Upon exiting the sorting system 10, the objects can be directed into any number of post-separation processes, shown generally at 39. For example, the separated objects from the system 10 that are to be retained can be delivered to a polymerase chain reaction (PCR) amplification reactor. In one embodiment, the PCR amplification reactor can be connected to the microfabricated chip. Alternatively, the separated objects from the system that are to be retained can be delivered to a microarray chip including either DNA, cDNA, mRNA, oligonucleotides, peptides, proteins, antigens or antibodies in discrete arrays prepared for hybridization and/or binding interaction experiments.

Figure 1B:
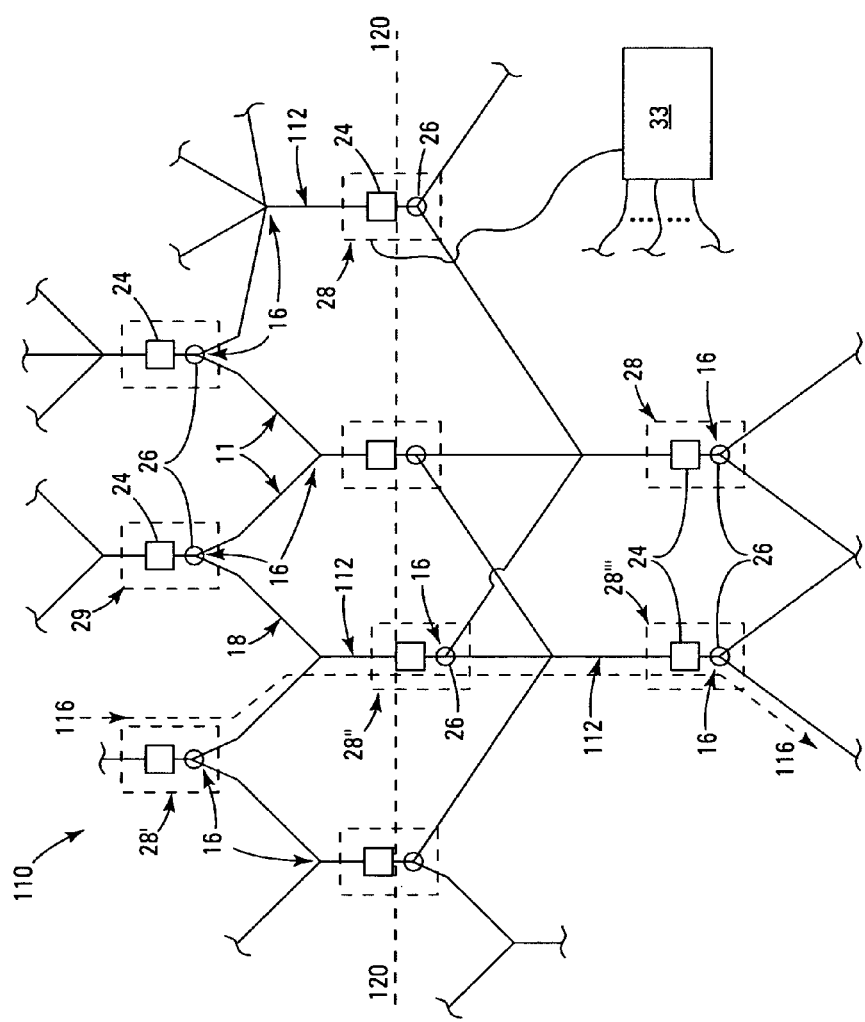
FIG. 1B shows a schematic of a multiple pathway object sorting system according to one embodiment of the present invention.

FIG. 1B shows an additional embodiment of the multiple pathway sorting system 110 according to the present invention. The multiple pathway sorting system 110 includes a pathway network 11 comprising a plurality of pathways 18 through which the fluid composition can be received and transported. Also as discussed herein, the system 110 can include a fluid manifold containing fluid and one or more makeup fluid ports, and the fluid composition includes the plurality of objects (e.g., cells).

The pathway network 110 shown in FIG. 1B includes one or more branch points 16. The multiple pathway sorting system 110 also includes one or more analyzer devices 24, as described herein, at one or more positions along the pathways 18 for use in analyzing one or more of the plurality of objects that flow in the pathways 18. In addition, the system 110 further includes one or more fluid flow controllers 26, as described herein. As discussed herein, the fluid flow controller 26 can be associated with at least one of the branch points 16, where the fluid flow controller 26 operates to direct at least one of the plurality of objects in the fluid composition through the branch points 16 based on the analysis of the objects.

In contrast to the system 10 described herein, the system 110 shown in FIG. 1B does not necessarily continually branch out into progressively greater numbers of pathways 18. Rather, the system 110 provides an example in which two or more pathways 18 coming from a branch point 16 can be coupled to form a single pathway 112. The fluid composition in the single pathway 112 can then move past the analyzer device 24 and through the branch point 16 under the direction of the fluid flow controller 26 (where the associated analyzer device 24 and the fluid flow controller 26 form the sorting module 28).

As will be noted in FIG. 1B, branch points 16 can provide parallel pathways from a branch point 16. As seen in FIG. 1B, the pathway entering the branch point 16 is a single combined pathway 112. In turn, the single combined pathway 112 can be provided by pathways 18 from a plurality of branch points 16 upstream of the resulting combined pathway 112. In other words, two or more pathways can combine to form the combined pathway 112. The resulting combined pathway 112 allows the fluid composition to move through the sorting module 28. The sorting module 28 can then direct one or more of the objects in the fluid composition into one or more parallel pathways 18 that extend from the branch point 16 based on the analysis of the objects.

With respect to the use of the phrase parallel pathways, it is understood that the concept of parallel pathways according to the present invention does not necessarily mean that the pathways emanating from a branch point 16 are physically parallel to each other. Rather, parallel in the context of the present invention include generally pathways 18 that extend from a common branch point. For example, the actual geometry used might be quite different to produce a smaller more efficient overall packaging size. Such geometry may extend to a third dimension.

The pathway network 11 shown in FIG. 1B also includes one or more branch points 16 in a series of pathways, where the series of pathways is shown generally at 116. In the series of pathways 116, each branch point 16 from the series of pathways has at least one analyzer device 24 and at least one fluid flow controller 26 associated therewith (forming the sorting module 28) to allow for a sequential analysis and sorting of objects through a progression of branch points.

So, for example, the series of pathways shown generally at 116 can begin at sort module 28', where the objects are analyzed and sorted through the branch point 16 via the fluid flow controller 26 based on the analysis of the objects. Next in the series of pathways 18, the object, or objects, are directed to sorting module 28". At sorting module 28" the objects are once again analyzed and further sorted through the branch point 16 via the fluid flow controller 26 based on the analysis of the objects. Again, the object, or objects, are directed to sorting module 28''' in the series of pathways 116. At sorting module 28''' the objects are again analyzed and further sorted through the branch point 16 via the fluid flow controller 26 based on the analysis of the objects. This type of sequential analysis and sorting can continue as needed until the desired level of sorting is achieved. Further, for example, objects of a similar type may be sorted by 29 and combined with those sorted by 28 for further sorting.

Similarly, each of a plurality of branch points 16 having at least one analyzer device 24 and at least one fluid flow controller 26 associated therewith can provide for a parallel analysis and sorting of objects simultaneously. The parallel analysis and sorting of objects is generally shown at 120. As previously discussed, the analyzer device 24 and the fluid flow controller 26 can be associated to form the sorting module 28. As shown in FIG. 1B, the sorting module 28 also includes the branch point 16. Groups of the sorting modules 28 can be arranged and operable for parallel analysis and sorting of objects. Each group of sorting modules forms a sort stage, where the sorting system preferably includes two or more sort stages. This concept was generally described herein in the discussion for FIG. 1A. As will be appreciated, sorting need not occur at every sorting module 28 in either the sequential and/or parallel analysis.

The sequential and parallel analysis and sorting described herein can provide for a progressively finer and finer sorting of objects (i.e., enrichment of the objects of interest). In other words, the system and method of the present invention can be used for a gradual examination of potentially multiple objects in a bolus of examined fluid in early stages and a gradual process of refinement to allow single desired object measurements at the later sorting stages. This feature is one of the reasons the present invention can operate at higher total throughput than devices requiring single cell analysis at all stages. The principle is that any time a signal can be obtained above background, a sort decision can be made which then spreads the volume out so that more volume containing only background can be removed at the next stage. Hence the signal-to-noise ratio is improved at each stage by keeping the signal and removing background at each successive stage.

For example, in a first sort level of a sequential analysis, the sorting modules 28 can be used to identify and sort a group of multiple objects in a bolus of fluid. In this early sort level, the measurements taken by the analyzer devices 24 can be taken on multiple objects, where the objects of interest may only comprise a fraction of the entire group of multiple objects. When the objects of interested are detected, the multiple objects are directed to subsequent sort levels. At subsequent sort levels of the analysis, the sorting modules 28 can be used to cause the fraction of objects of interest to become progressively higher (i.e., as the sorting progresses there is enrichment of the objects of interest). As discussed herein, the use of progressive sort levels can be used to achieve the desired level of sorting of the objects, where it is possible that downstream sort levels having multiple parallel sorting modules can be used to analyze and sort individual objects.

The system 110 shown in FIG. 1B can also include a fluid manifold containing the makeup fluid and one or more makeup fluid ports, as discussed herein. In addition, the system 110 further includes a control apparatus 33. As discussed, the control apparatus 33 receives measurement signals from at least one analyzer device 24 and determines at least one characteristic of an object based on the measurement signal(s). It should be understood that the results of analysis of earlier analyzer stages can be combined with the new analyzer results to produce a sort result based on the entire history of the objects analysis down its multi-step pathway. Thus, a sort decision at a branch may use not only the analyzer measurement at that branch point but also, if desired, all of the previous measurements or decision points made on that object during its entire history in the device. In response, the control apparatus 33 can then provide a control signal to one or more of the fluid flow controllers 26 based on the at least one characteristic of the object.

Figure 1C:
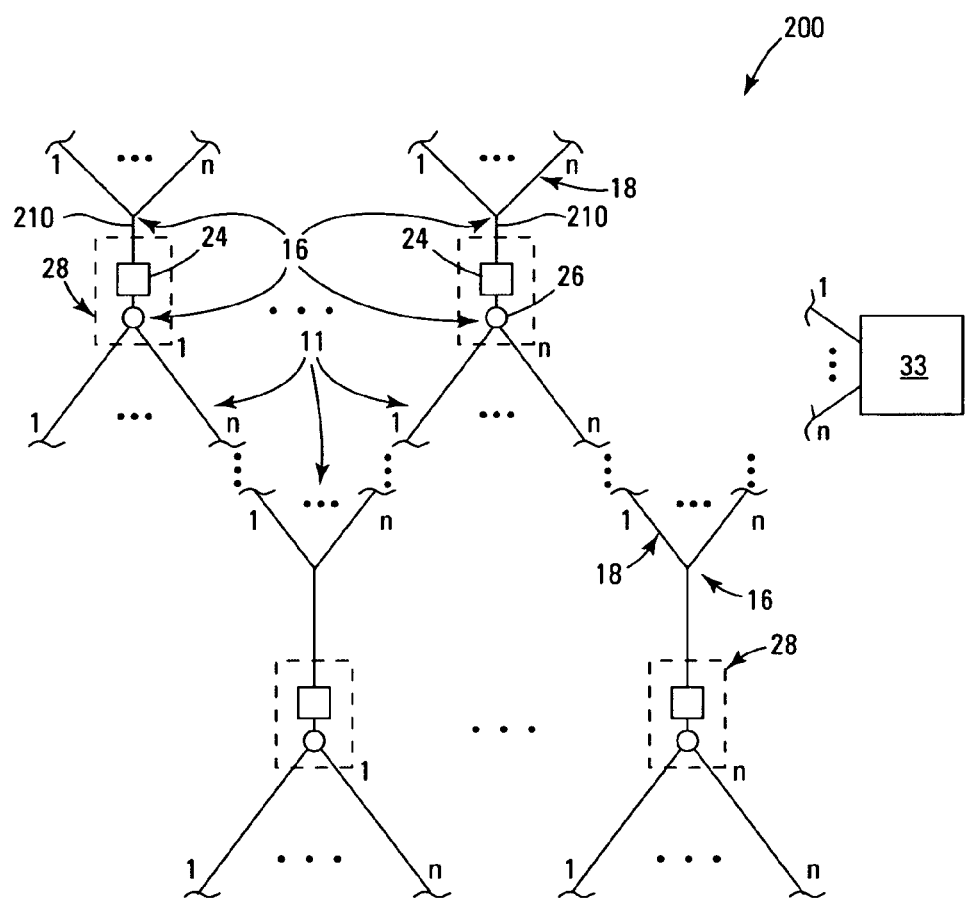
FIG. 1C shows a schematic of a multiple pathway object sorting system according to of the present invention that generalizes at least the embodiments shown in FIG. 1A and FIG. 1B.

FIG. 1C shows an embodiment of a multiple pathway sorting system 200 according to the present invention that generalizes at least the architecture of FIGS. 1A and 1B. The multiple pathway sorting system 200 includes a pathway network 11 comprising a plurality of pathways 18 through which the fluid composition can be received and transported. As discussed herein, the system 210 can also include a fluid manifold containing fluid and one or more makeup fluid ports.

The pathway network 11 shown in FIG. 1C includes separately one to n (where n is an integer value larger than one) branch points 16, pathways 18, and sorting modules 28 (and the associated analyzer devices 24 and fluid flow controllers 26). As a result, the multiple pathway sorting system 200 can be configured with any number of sorting modules 28 arranged in any serial or parallel fashion having any number of branch points 16 either feeding (via the single pathway 210) or emanating from the sorting module 28.

The system 200 shown in FIG. 1C can also include a fluid manifold containing the makeup fluid and one or more makeup fluid ports, as discussed herein. In addition, the system 200 further includes a control apparatus 33. As discussed, the control apparatus 33 receives measurement signals from at least one analyzer device 24 and determines at least one characteristic of an object based on the measurement signal(s). In response, the control apparatus 33 can then provide a control signal to one or more of the fluid flow controller 26 based on the at least one characteristic of the object.

The present invention can be used in sorting and/or counting any number of specific cell types from a mixed population of cells. For example, this can include sorting and/or counting infectious biological objects from non-infectious biological objects, e.g., live HIV-infected mammalian stem cells (e.g., human cells), T-cells and lymph node cells for monitoring H117V infection and AIDS infection, isolation of rare cells, such as live, viable human stem cells suitable for transplantation, with simultaneous purging of tumor cells from peripheral blood and bone marrow for subsequent autologous stem cell transplantation; sorting of live, HIV-infected T-cells and lymph node cell subsets; bacterial clones containing libraries of human immunoglobulin epitope sequences for recombinant vaccine development against pathogens; and isolation of cell subsets for subsequent gene expression analysis on cDNA microarrays. The separation of tumor cells from normal cells for gene expression analysis in cancer research and for monitoring the progress of chemotherapy; sorting of chromosomes prior to sequence analysis; monitoring of CD4+ T-cells to track progress of AIDS infection and efficacy of HIV vaccine trials, and military applications to sorting of biohazardous organisms.

In addition, the present invention could be used in identifying, sorting and/or collection of tumor vs. normal cells for subsequent gene expression profiling of the cells for basic research and for monitoring the progress of chemotherapy. Also, the present invention could be used in identifying, sorting and/or collection of bacterial clones containing libraries of human immunoglobulin epitopes, for development of recombinant vaccines.

Furthermore, the present invention could be used in sorting CD34-positive human stem/progenitor cell line (KG1 cells) from human CD34-negative T-cells (CEM cells). In addition, it may be possible to use the present invention to sort CD34+/CD38+/CD4− cells from mobilized human stem/progenitor cells obtained by apheresis. In an additional example, the present invention could be used to purge human tumor cells from blood and bone marrow cells. For example, sorting a cell mixture of human T-cells (CEM cells) from human breast cancer cells (MCF-7 cells).

As will be appreciated, the present system could be used to provide cell sorting down to single cell level, where the cells can be distinguished on the basis of HLA-DQα DNA typing through the use of PCR. In a further example, the present invention can be used to sort HIV-infected cell subsets. For example, the HIV sorting assay can start with a human T-cell line (8E5 cells) that was originally infected with HIV-1, but now defective in production of infectious virus. In a further example, the present invention can be used to sort bacteria containing human DNA sequences. In addition, the present invention can be used to sort cells for subsequent cDNA microarray analyses. For example, the present invention can be used to sort purified cells for subsequent microarray analyses.

Figure 4:
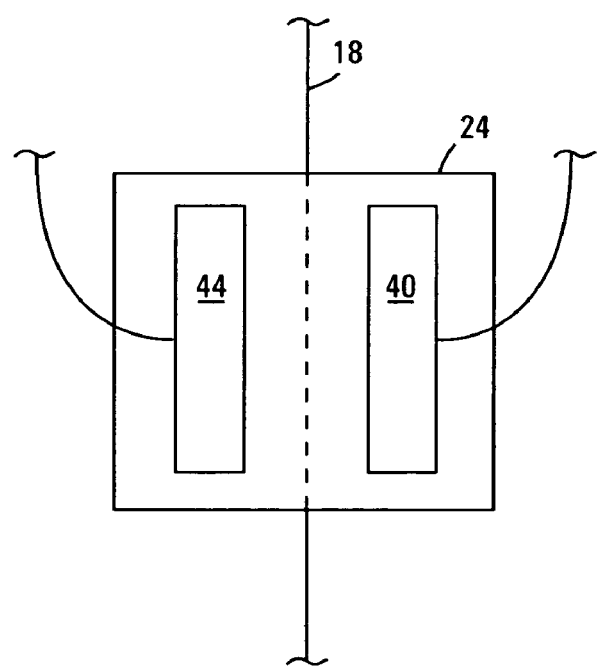
FIG. 4 shows a general schematic of one embodiment of an analyzer device for use in a sorting system, such as shown in FIGS. 1A-C, according to the present invention.

FIG. 4 shows a generalized view of one embodiment of an analyzer device 24 such as that used in the sorting systems of FIG. 1A-1C. The analyzer device 24 can include one or more exciters 40 and one of more detectors 44. For example, the one or more exciters 40 can provide electromagnetic energy to the fluid composition in the pathway 18, and the objects therein. Energy returned by the objects can be detected and measurements representative of one or more characteristics of the objects based on the detected energy can be made for use in sorting the objects. For example, absorption of light by the objects can be in any number of different ranges of the electromagnetic spectrum including but not limited to, the visible portion of the electromagnetic spectrum (400-700 nm), the ultraviolet portion of the electromagnetic spectrum (200-400 nm), and the near-infrared portion of the electromagnetic spectrum (700-900 nm).

One or more different exciters 40 may be used in the analyzer device 24. For example, the exciters may include individually-addressable light emitting diodes (LED), laser diodes, organic light-emitting diodes (OLEDS) (e.g., those that could be "printed" directly onto the fluidic substrate using ink-jet printing of optical components), and VCSELS (vertical cavity surface emitting lasers). Of these, the VCSEL are preferred due to the spatial density of individually addressable elements.

In addition, it is possible to use compact arrays of VCSELS, for which various visible light wavelengths are possible. The advent of inexpensive excitation sources now allows these excitation sources to be distributed throughout an arrayed, parallel fluid processing structure which then permits much higher throughputs and also multiple sort decisions sequentially over time.

Examples of detectors 44 for use in making measurements representative of characteristics of the objects include, but are not limited to, a charge-coupled device (CCD) array (e.g., linear or other) detector (e.g., the CCD detector arrays can have more than one detector pixel for optical interrogation of the objects flowing through the pathways), photosensitive diodes or resistors, such as silicon photodiode detectors and light-sensitive MOSFET devices.

In addition to their small size and low cost, CCD's have the advantage that their outputs can be very rapidly processed by digital signal processing in a variety of ways including integration and signal averaging. Depending on the detector design, pixel readout frequencies of 10 Mpixel/s, or even 100 Mpixel/s on off-the-shelf line-scan (i.e., single line) CCD's with multiple outputs are possible. The use of CCD's as detectors also allows some degree of imaging of the object either as it flow past or is temporarily captured during stop-flow conditions. This permits some measure of object morphology. The analog-to-digital converter is used to interface the detectors 44 (e.g., the CCD) to the computer 34 included in the control apparatus 33.

Further, miniature "painted" single pixel or single diode filters could be used to detect one or more colors within a single CCD, thus maximizing the detection capabilities and minimizing the size of each detection point. Any number of excitation and emission detection components and selected components could be selected that work suitably for the present invention. For example, it is possible to use a three or four-color LED mini-array that can allow for three- or four-color fluorescence sorting of the objects, where results from multiple sources can be combined by Boolean logic to select the desired cell type. These optical components can be integrated onto microchips to allow for construction of a high speed sorter within a small, closed package that would be compatible with use in biohazard hoods, space research and field use.

In yet another example, the detectors 44 can include small LED's as exciters and one or more CCD's to measure light scattered from the cells. LED's, and laser diodes, are available now for a wide range of wavelengths including but not limited to those that can excite common cytometry probes at 405 nm, 447-480 nm, 490-525 nm, 532 nm, 620 nm, 635 nm, 650 nm, 670 nm, 670-686 nm, 750-870 nm. Using fiber-optic technologies, it is possible to multi-furcate a single laser into a number of light paths so that even a single laser could be used to provide spatially separated excitation sources at many different points in an arrayed fluidic structure such as described in this invention.

Further, another detection technique that may be used for taking measurements and classifying objects flowing through the pathways is based on the induced luminescence of components as they flow through the pathways. Examples of induced luminescence useful with the present invention include induced fluorescence, induced phosphorescence, and induced chemiluminescence of the objects passing through the pathways. The chemiluminescence of the objects passing through the pathways can be implemented by on-chip addition of chemiluminescent-inducing reagents to the objects flowing through the pathways. In the case of chemiluminescence it is possible to produce signals from objects without an optical excitation source.

In yet another embodiment, classifying objects flowing through the pathways can be based on the use of the optically-determined morphology of the objects as they pass through the pathways. Examples of classifying objects based on the optically-determined morphology include those that use CCD-image analysis. In addition, classifying objects flowing through the pathways can further be based on the use of the magnetic or paramagnetic properties of the objects as they pass through the pathways. Finally, any of the aforementioned techniques (e.g., light absorption, spontaneous or induced light emission, magnetic or paramagnetic properties, or morphologic properties) used for classifying objects passing through the pathways can be used in any possible combination for classifying the objects.

As discussed herein, one or more types of measurements can be made on the objects as they move through the pathways. Examples of multiple types of measurements include, but are not limited to, fluorescence at multiple wavelengths, which can be made at a given detector using CCD array filter masks so that different array elements read fluorescence at different wavelengths. In addition, multiple types of measurements taken can be used to determine the velocity of the objects as they move through the pathways 18 (e.g., a pair of laser diode-CCD fluorescence could be used to detect both the presence and the velocity of labeled cell(s)). In addition to velocity, relative or absolute object size and shape can be measured using a variety of existing pulse width and pulse rise-time "time-of-flight" techniques.

Figure 5:
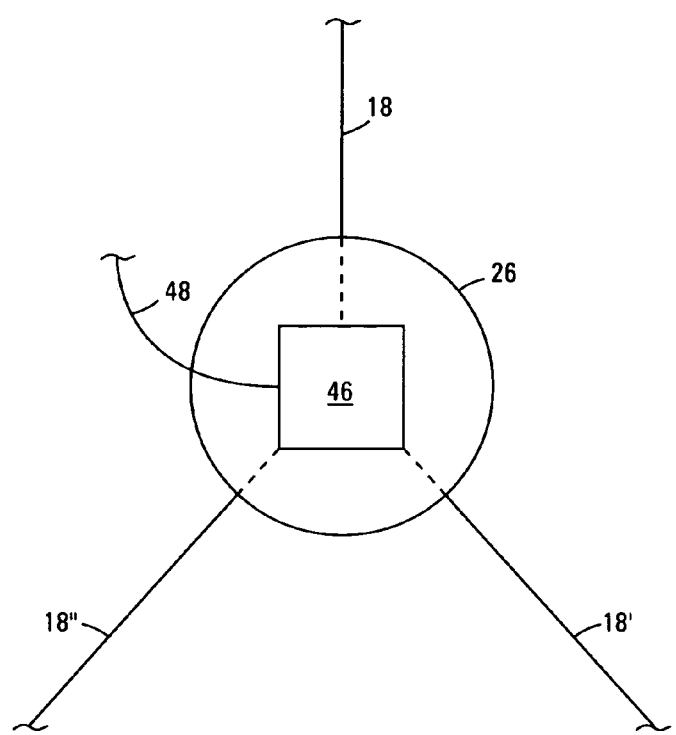
FIG. 5 shows a general schematic of one embodiment of a fluid flow controller for use in a sorting system, such as shown in FIG. 1A-C, according to the present invention.

FIG. 5 shows a general view of the fluid flow controller 26 discussed herein that can be used in a sorting system such as shown in FIG. 1. The fluid flow controller 26 can include any number of mechanical and/or electromagnetic devices 46 to allow for directing the flow of the fluid composition in the pathway based on a signal from the analyzer device 24 and/or the controller apparatus 33 via link 48. For example, the opening or closing of one or more mechanical valves based on a signal from the analyzer device 24 and/or the controller apparatus 33 can be used to direct the fluid composition and objects into one pathway or another at a branch point 16.

As discussed herein, directing fluid flow can include stopping fluid flow in one or more pathways 18 at a branch point 16, while allowing fluid flow to continue down other pathways from the same branch point 16. This possibility of stopped flow analyses allows applications not possible on a conventional flow cytometer/cell sorter since in general the flow rate must be fairly continuous, especially if droplets are being generated and maintained for droplet-based sorting.

Figure 6A:
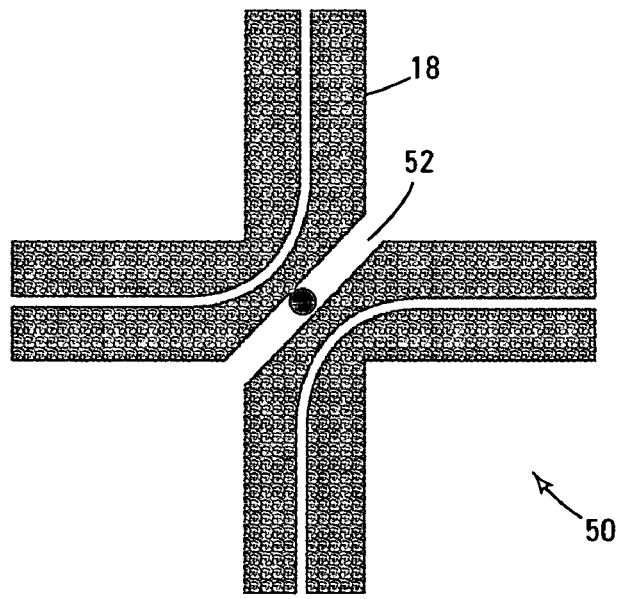
FIG. 6A, FIG. 6B, and FIG. 6C show general schematics of embodiments of a fluid flow controllers shown generally in FIG. 5 for use in a sorting system, such as shown in FIG. 1A-C, according to the present invention.
Figure 6A:
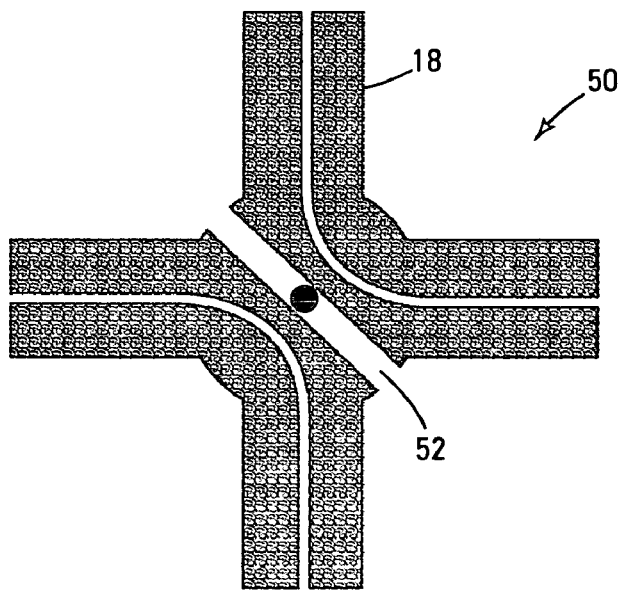
Figure 6B:
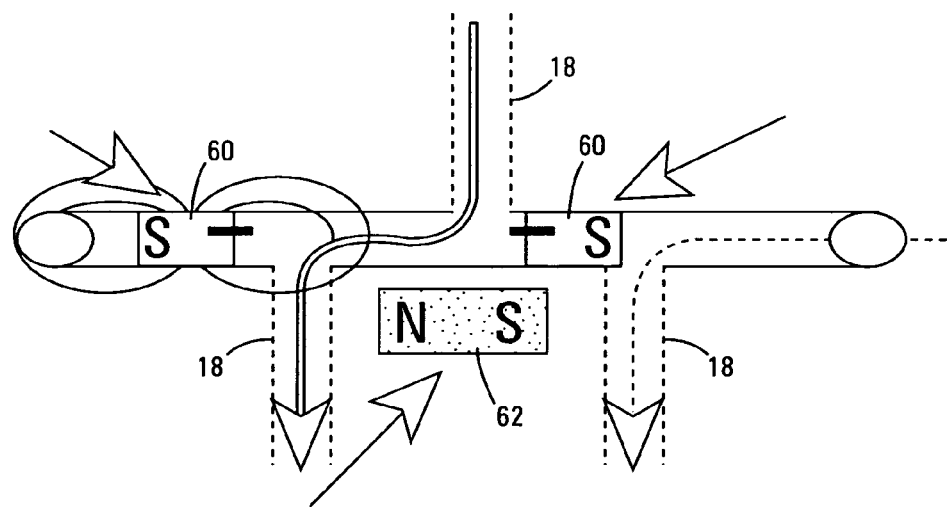
Figure 6B:
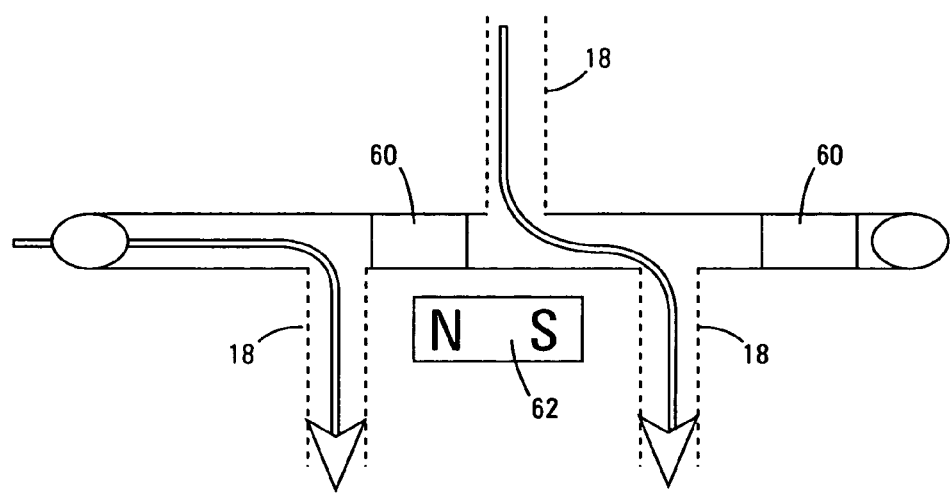
Figure 6C:
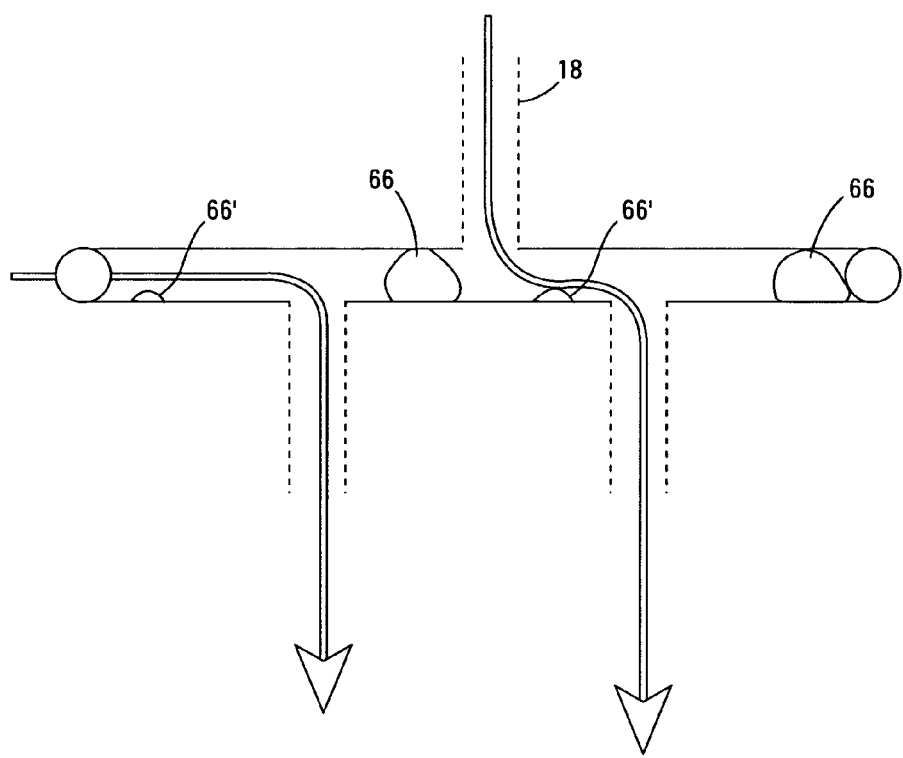

Various fluid flow controllers 26 may be used, such as for example, those shown in FIG. 6A, FIG. 6B and FIG. 6C. For example, FIG. 6A provides an example of a rotary valve 50. The rotary valve 50 can include a vane 52 that can be positioned so as to direct the fluid composition flowing in the pathway 18. In one embodiment, the vane 52 of the rotary valve 50 can be positioned through the use of a rotary solenoid (or stepper motor, or servo motor) and can direct the flow of the fluid composition under the control of the analyzer device 24 and/or the control apparatus 33.

In an additional embodiment, the device 46 used in the fluid flow controller 26 can include other types of mechanical valves integrated into the pathways at or adjacent to the branch points of the n-furcations. For example, different valve types can also include electromagnetically activated valves and/or inflatable elastomer valves. It should be understood that the combination of serial and parallel architecture of the present invention allows it to operate with total throughput rates far in excess of the limitations of fluidic switching speeds imposed by a conventional single station sort decision device. Hence, even with individual station fluidic switching rates of a millisecond, total object throughput rates of more than one million objects per second can be obtained with this invention with high yield and purity of sorted objects.

FIG. 6B provides an example of electromagnetically activated magnetic shuttle valve 58. The magnetic shuttle valve 58 can include magnetized plugs 60 (e.g., plugs having magnetic materials embedded therein) that can be slid within the pathway 18 under the influence of a magnetic field. The magnetic field used to slide the magnetized plugs 60 can come from any number of sources. For example, an electromagnet 62 can be used to slide the magnetized plugs 60 to open one pathway and close another pathway. In one embodiment, the electromagnet 62 of the magnetic shuttle valve 58 can be energized so as to direct the flow of the fluid composition through the pathways 18 under the control of the analyzer device 24 and/or the control apparatus 33.

FIG. 6C shows an additional example of a valve useful with the fluid flow controller 26 of the present device. FIG. 6C provides an example of elastomeric valves 66 and 66'. The elastomeric valves 66 and 66' can be integrated into the pathway 18 at predetermined positions to allow for one or more of the pathways 18 to be closed, while other pathways 18 are kept open.

For example, in FIG. 6C elastomeric valves 66 are shown as being closed (e.g., valves 66 are inflated), while elastomeric valves 66' are shown as being open (e.g., valves 66' are deflated). In this situation, the elastomeric valve 66' is closed by inflating the valve and opened by deflating the valve. In one embodiment, the elastomeric valves 66 and 66' can have an expandable wall that can be used to block the pathway 18 in the inflated position and allows for fluid flow when in a deflated position. For example, the elastomeric valves 66 and 66' can be inflatable "micro-balloons" having an inflation port to allow for inflation (valve closing) or deflated through the introduction of a fluid or gas into the balloon under the control of the analyzer device 24 and/or the control apparatus 33.

Figure 7:
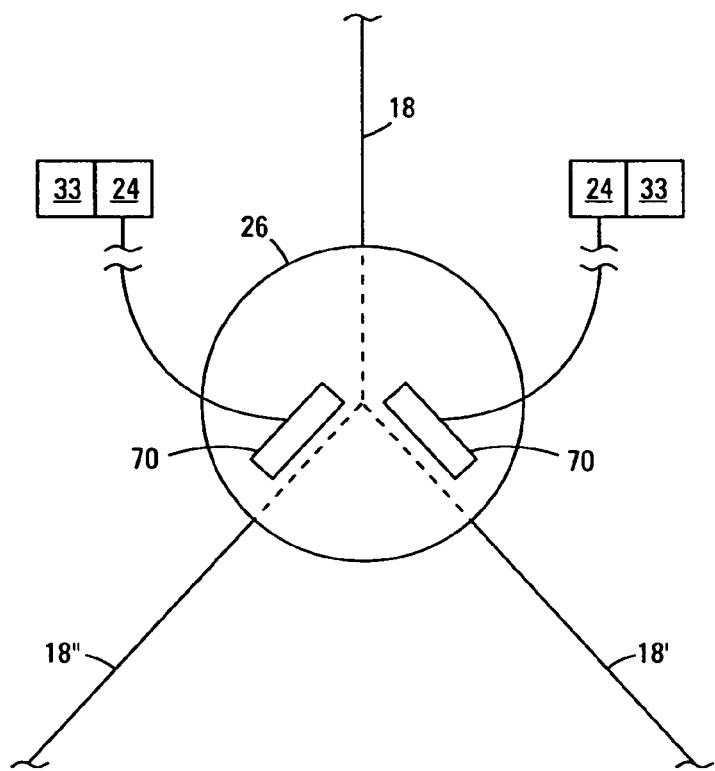
FIG. 7 shows another general schematic of another embodiment of a fluid flow controller generally in FIG. 5 for use in a sorting system, such as shown generally in FIG. 1, according to the present invention.

FIG. 7 shows an alternative embodiment for the fluid flow controller 26 discussed herein. In the present embodiment, the fluid flow controller 26 can include any number of devices 46 to allow for directing the flow of the fluid composition into one pathway or another at the n-furcations of pathways 18 based on a signal from the analyzer device 24 and/or the control apparatus 33. Examples of this include devices that are able to generate electro-osmotic forces and/or electrophoretic forces to act upon the fluids and the objects flowing through the pathways. In an alternative embodiment, application of an electromagnetic field influencing fluid and constituent object movement can be used to direct magnetic objects or substances, including the fluid itself, within the pathways into one pathway or another at the n-furcations of pathways. In addition, piezo, thermal, or magnetorestrictive induction of perturbations in the fluid flow can also be used to direct selected objects or volumes of fluid into one pathway or another.

When electromagnetic fields are used in the present invention, the fluid composition can include nano-size magnetic particles at a concentration sufficient to allow the fluid composition to be influenced (i.e., directed) through the application of the electromagnetic field. As used herein, the fluid composition containing the nano-size magnetic particles can be referred to as a ferrofluid. When the ferrofluid of the present invention is used, force vectors from applied magnetic fields can be used to move the ferrofluid down the pathways of the fluid architecture system. In addition, the force vector from the magnetic fields can control the speed and ultimate movement of fluid to any location in the system, including holding the fluid and objects stationary for further measurements (e.g., closing one or more pathways 18 using the ferrofluid).

As an alternative to use of the ferrofluid, the targeted cells for sorting and enrichment could be labeled with magnetic markers, usually with monoclonal antibodies that include magnetic particles.

Different ferrofluids can be selected for use with different object types for different types of applications. For example, bacterial and mammalian cells can have different responses to a given ferrofluid. The general criterion is that the ferrofluid be biocompatible in terms of cell viability and growth. The ferrofluids also need sufficient magnetic moments to allow rapid fluidic switching at reasonable electromagnetic field strengths. If necessary the assembly can be cooled with coolers to dissipate heat if heat from the electromagnets become high enough to represent a heat problem.

As shown in FIG. 7, the fluid flow controller 26 includes pathway 18 that enters the fluid flow controller 26 and bifurcates into two pathways 18' and 18". Electromagnetic valve units 70 are positioned along the pathways 18' and 18". The electromagnetic valve units 70 help direct the flow of the ferrofluid through the fluid flow controller 26 based on a signal from the analyzer device 24 and/or the control apparatus 33. For example, the analyzer device 24 and/or the control apparatus 33 can be used to control the electromagnetic valve units 70 to stop and/or slow flow down one pathway (18' or 18") under an imposed magnetic field, while allowing ferrofluid flow through the other pathways (18" or 18'). Thus, at these n-furcation points, flow is completely controlled by electromagnets, which pull the fluid down one pathway or the other, depending on which electromagnet is on.

An important criteria for use of the ferrofluid in the present invention is that the ferrofluid have sufficient magnetic moment to be pulled into the desired pathway using relatively small electromagnets. In addition, the ferrofluid must have low enough absorbance and auto-fluorescence to allow fluorescence analysis of the objects, as discussed herein. In addition, the ferrofluid need to have low enough viscosity to allow movement through the pathways (e.g., about a 1 cP). Finally, when cells are to be sorted and recovered, the ferrofluid must be non-toxic to the cells and readily separable from the sorted and recovered cells.

To a first approximation the force of magnetism on the ferrofluid will be proportional to the intensity of Magnetization M of the ferrofluid material, and how the magnetic field strength H varies. The ferrofluid can be directed down a pathway from a branch point. So, not only can the magnetic fluid be pulled left or right, but if desired, the fluid can be pulled down the pathway at a controllable velocity. The degree to which a ferrofluid is moved under the force of the applied magnetic field can be varied within the limits of the ferrofluid composition, which makes the choice of ferrofluid important. However, the applied magnetic field strength can also be increased or decreased to control the total force.

Figure 8:
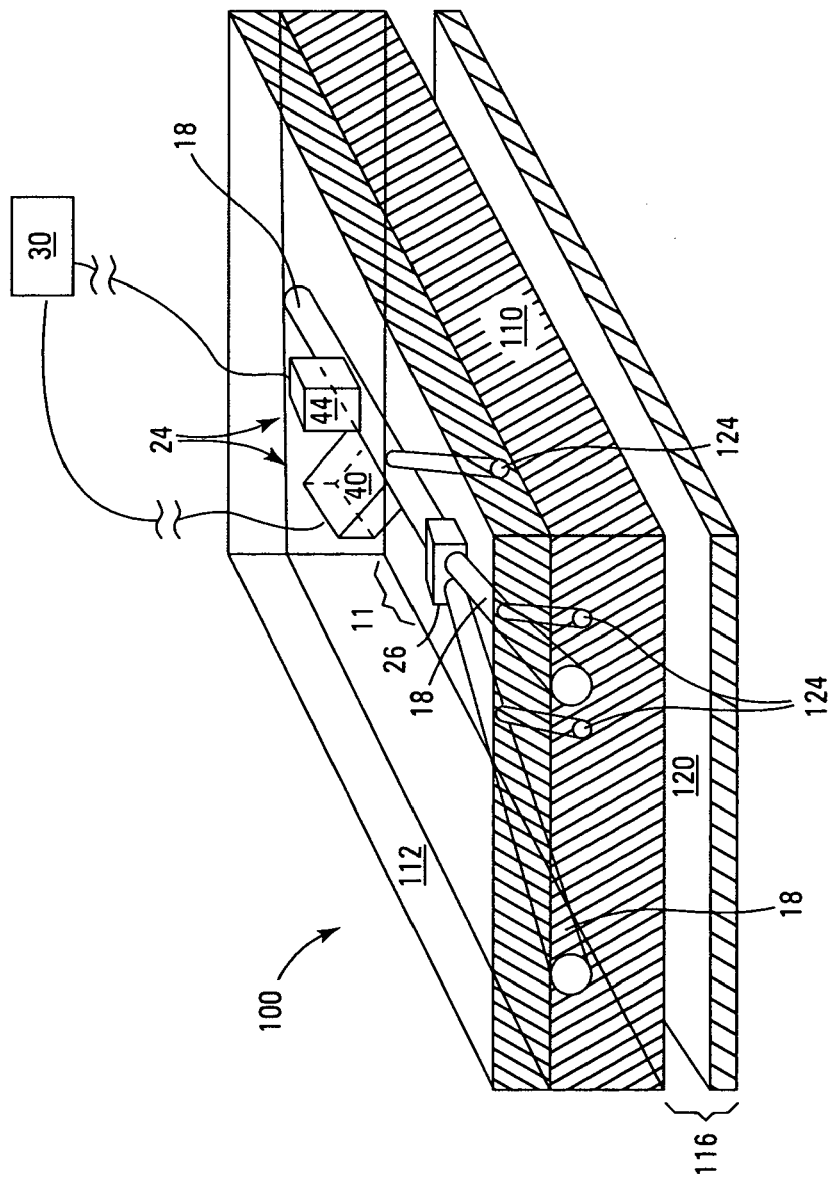
FIG. 8 shows a perspective view of one embodiment of a portion of a sorting system, such as shown in FIG. 1A-C, according to the present invention.

FIG. 8 shows one exemplary embodiment of a portion of a sorting system 100 of the present invention formed using conventional planar microstructure approaches. For example, these conventional planar microstructure approaches can include, but are not limited to, laser-etched pathways 18 cut into a plate 110, with a cover plate 112 to enclose the pathway 18. It is understood that the pathways 18 shown in FIG. 8 represent only a portion of a larger pathway network 11 that includes sorting modules, such as that shown in FIGS. 1A-1C.

Preferably, the pathways 18 of the present invention have a diameter or cross-section dimension within the range of about 50-2000 microns. As discussed herein, the cross-sectional dimension of the pathways 18 can remain essentially constant through out the pathway network 11 of the system 10, where makeup fluid is used to maintain a suitable pressure through out the pathway network 11. Alternatively, the cross-sectional dimension of the pathways 18 can change (e.g., become smaller) progressively along the pathway network 11 of the system 10 to ensure a suitable pressure for moving the fluid composition through the pathway network 11 of the system 10.

The plates 110 and 112 are made of any number of materials that can be bonded together (e.g., in a "pancake stack" by pressure-set and/or thermal-set bonding, which will allow rapid and precise alignment and fabrication). For example, polymer materials having suitable processing and optical characteristics can be used for the plates 110 and 112. Examples of such polymer materials include, but are not limited to, polyamides or polycarbonates. Other polymer materials having the recited characteristics are also known.

In addition, the components of the system 100 (e.g., plates 110 and 112, pathways 18, etc.) form a fluid tight system (i.e., the system 100 is sufficiently sealed to prevent fluid leaks from the pathways 18). Sealing the plates 110 and 112 of the system 100 is an important aspect for using the system 100 for separation of bio-hazardous materials.

The system 100 also includes a full-system manifold 116 that lies beneath the system 100. The full-system manifold allows "makeup" fluid 120 to be ported directly into the system 100 at all levels, with no pressure drop. This structure requires running vias 124 (e.g., vertical vias drilled through the plate 110 of the system 100) into the makeup fluid 120 lying below. The benefit, however, is that makeup fluid 120 can be delivered into the system 100 at all levels with uniform pressure and flow.

The system 100 can further include an analyzer device 24 and a fluid flow controller 26, as discussed herein. The analyzer device 24 can include one or more exciters 40 and one of more detectors 44. In the present example, the exciters 40, such as LED or diode laser sources, can be attached to the system 100 (e.g., to provide excitation in a direction perpendicular to the etched pathway 18). The cover plate 112 has good optical qualities (e.g., has relatively high transmission) to allow excitation waves from exciter 40 to be transported therethrough to the fluid composition in the pathway 18. The one of more detectors 44, such as a CCD array, may be optically coupled to the cover plate 112 for providing measurements representative of one or more characteristics of the objects in the pathway 18 (e.g., reflected light). This construction allows for ready access of the electronic devices for coupling to the control apparatus 33 (e.g., computer 34) for software control. This "sandwich" design allows for use of interchangeable or inexpensive disposable fluidic channel planar arrays sandwiched between exciter and detector levels. It should be understood that such a planer array could be multiplanar through the appropriate stacking of multiple planar arrays producing a three-dimensional sandwiched structure. This modular approach also allows for changing or upgrading of the exciter or detector layers, leading to a flexible overall design.

The fluid flow controller 26 can include any flow switching structure or technique discussed herein. For example, fluid flow controller 26 can be a valve structure (e.g., rotary valve) having a solenoid switch under control of the analyzer device 24 and/or control apparatus 33.

Figure 9:
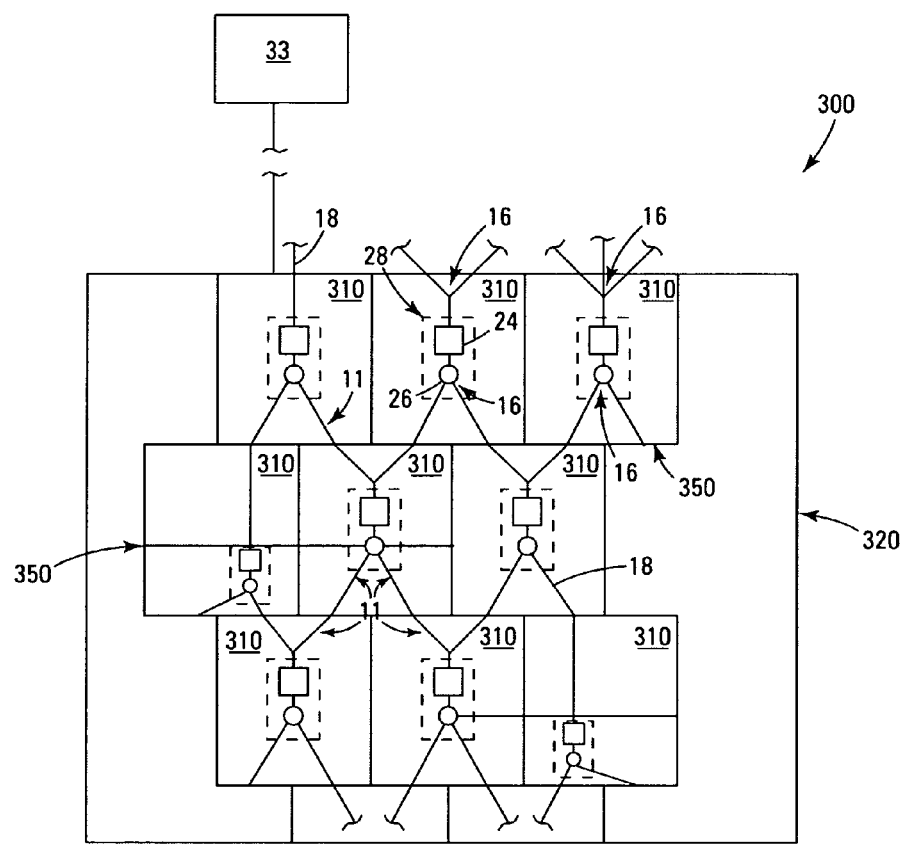
FIG. 9 shows a schematic drawing of one embodiment of a sorting system having interconnecting separate branch point modules in a holding frame according to the present invention.

FIG. 9 shows an additional embodiment of a sorting system 300 according to the present invention. The sorting system 300 includes a pathway network 11 that includes a plurality of pathways 18. As with the other systems described herein, the pathways 18 of the network 11 are operable to receive the fluid composition that includes the plurality of objects. The pathway network 11 includes one or more branch points 16, as described herein. Also as discussed herein, the system 300 can include a fluid manifold containing fluid and one or more makeup fluid ports.

FIG. 9 also shows a plurality of separate branch point modules 310. In one example, the separate branch point module 310 includes at least one branch point 16 and at least portions of the pathways 18 associated with the branch point 16. The separate branch point modules 310 are configured to be assembled, including reversibly assembled, for use as at least a portion of the pathway network 11. As shown in FIG. 9, the pathway network 11 can include two or more of the separate branch point modules 310 that are assembled end-to-end and/or side-to-side in such a way to form a fluid tight seal between any and all pathways 18 thereby extending the length of the desired pathways 18.

The separate branch point module 310 also includes one or more analyzer devices 24 associated therewith, where the analyzer device 24 (as previously described) can be used in analyzing one or more of the plurality of objects that flow in the pathways 18. In addition, the separate branch point module 310 includes one or more fluid flow controllers 26 that are operable to direct fluid composition therein. As discussed, analyzer devices 24 and the associated fluid flow controller 26 form sorting module 28. Examples of separate branch point modules 310 are provided in FIG. 9, where each example can have a different combination of pathways 18, branch points 16, and sorting modules 28, where the sorting modules can include any number and type of analyzer devices 24 and fluid flow controllers 26 described herein. Thus, a plurality of detection and selection arrays may be assembled from the separate branch point modules 310.

As illustrated in FIG. 9, two or more separate branch point modules 310 can be configured (i.e., assembled together) for use as at least a portion of the pathway network 11. In one example, the two or more branch point modules 310 are configured to be inserted into a holding frame 320 for use as at least a portion of the pathway network. In one example, the holding frame 320 has a planar surface on which the coupled separate branch point modules 310 may be placed.

The planar surface of the holding frame 320 serves to help properly align the pathways 18 of the separate branch point modules 310 prior to their coupling. The holding frame 320 also serves to support the separate branch point modules 310 once coupled. The pathways 18 of the separate branch point modules 310 making up the pathway network 11 are preferably coupled in a fluid tight manner.

Each separate branch point module 310 can have one or more of any of the previously described analyzer devices 24. As a result, each of the two or more separate branch point modules 310 that go into constructing a pathway network 11 may be configured with at least a portion of a different analyzer device 24 or no analyzer device at all. In addition, each separate branch point modules 310 can have the same or different pathway 18 (flow path) configurations than another of the branch point modules 310. The configuration of the pathway 18 for the separate branch point modules 310 can be selected to allow for any one of the previously illustrated pathway networks 11. So, for example, separate branch point modules 310 can be assembled to receive fluid composition from multiple branch points through multiple pathways and to provide fluid composition to one or more pathways. In addition, separate branch point modules 310, when assembled, can be used to receive fluid composition from a single branch point through a single pathway and provide fluid composition to one or more pathways 18. In addition, other pathway networks are possible.

In certain situations, arrays of separate branch point modules 310 may be constructed in which there are "dead end" pathways 350. These pathways 350 may be truncated in any manner, such as by the use of any means of blocking endplates or other interfering mechanisms to create the dead-end. The separate branch point modules 310 may be arranged in the holding frame 320 so as to serve as an integral component of an overall sorting system, where electrical, and fluid connections can being made through the use of contact points embedded in the frame 320 that align with corresponding contact points in the separate branch point modules 310. This allows the separate branch point modules 310 to be coupled to the control apparatus 33 for use in controlling the sorting of the objects in the fluid composition. The separate branch point modules 310 can be interconnected using any number of fluid tight connectors. For example, the connectors can include standardized fluid tight coupling such as a male-female coupling configuration. And, as discussed herein, the interconnections of modules need not be in the same plane but can be connected in additional layers creating an overall three-dimensional structure.

Based on the forgoing description, it may be possible to analyze and sort cell subpopulations using multi-sort modules and multistages at rates of greater than 40,000 cells/second (possibly up to 1,000,000 cells/second) in a closed system under safe biohazard containment conditions.

For a typical example of high throughput sorting, consider the sorting $10^7$ cells of a 10% cell subpopulation from $10^8$ total cells. The sample could be input at a concentration of $10^7$ cells per milliliter. At a sample introduction rate of 50 microliters per minute, the sort time will be approximately 20 minutes, producing 260 cells per second at each of the 32 parallel sort-modules (a 32 furcation) shown generally at the sorting stage 30 in FIG. 1.

If the fluidic switching at the fluid flow controller 26 is relatively slow, e.g. 10 milliseconds, the average fluid bolus sorted will contain 2.6 cells. The actual number can be calculated by queuing cell theory or approximated by Poisson statistics. For simplicity, assume that of the 2 to 3 cells per fluid bolus, only one cell is the cell of interest. So the purity of the sort at that branch point is $1/2.6$ or approximately 38 percent. By going down one additional sort level and sorting again, the cell of interest can be separated at virtually 100% purity.

The power of parallel processing and multistage sorting is readily apparent in this example, as the process would have sorted $10^7$ cells in 20 minutes at an average rate of over 83,000 cells per second.

In a second example, for the system and method of the present invention could be used for high speed sorting of rare cell subpopulations from a general cell population. For example, the present invention can be used in screening of bacterial libraries containing human immunoglobulin epitope sequences against an unknown pathogen for recombinant vaccine development. For example, the goal may be to find and isolate the 1 in 10,000,000 of the bacterial cells that will be fluorescently labeled (and could thus yield a vaccine). Starting with a concentration of bacteria of $10^9$ cells/ml and an initial flow rate of 1 ml/sec fluid input, about 1,000,000 cells per second will be processed in about 1000 seconds (17 minutes).

If the valve-switching time is set to 100 msec, then 100,000 cells would be selected in the first bolus of fluid. This bolus selection would occur, on average about once per 10 seconds, because an average of only 1 rare cell will pass by the detection optics each 10 seconds. This means the valve will be open for 100 msec and closed for 9900 msec, on average, out of every 10 seconds. This is a "valve open" duty cycle of about 1%. That in turn means that the fluid surrounding the first selected target cell will be diluted by about 99:1 after mixing in the additional volumes of makeup fluid in the first mixing station. Thus, exiting the mixing station, there will be, on average, approximately 100,000 cells for each 10 ml, or 10,000 cells/ml.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A flow sorting method comprising:
transporting a fluid composition comprising a plurality of objects through a pathway network, wherein the pathway network comprises a plurality of pathways and one or more branch points;
analyzing groups of multiple objects of the plurality of objects being transported in a pathway of the pathway network to detect objects of interest, wherein analyzing each group of multiple objects comprises analyzing simultaneously the multiple objects of the group together by providing a measurement taken on multiple objects of the group together in the pathway, the measurement for use in determining a pathway of the pathway network down which the group is to be directed; and
directing at least a few of the groups of the multiple objects through one branch point of the one or more branch points down at least one pathway of the plurality of pathways based on the analysis of the groups of multiple objects such that a distance between multiple objects of the few groups is increased and directing other groups of multiple objects down a pathway different than the at least one pathway to increase the percentage of objects of interest in the at least one pathway relative to other objects present therein, wherein the method further comprises:
analyzing objects of the few groups directed down the at least one pathway with increased distance between multiple objects thereof to detect objects of interest, wherein analyzing the objects of the few groups comprises analyzing simultaneously multiple objects together in a pathway by providing at least a measurement taken on the multiple objects together, the measurement for use in determining a pathway of the pathway network down which one or more of the objects of the few groups is to be directed; and
directing one or more of the objects of the few groups through another of the one or more branch points down another pathway of the pathway network based on the analysis of objects of the few groups to further increase the percentage of objects of interest therein relative to other objects present therein.

2. The method of claim 1, wherein transporting the fluid composition comprises repeatedly separating the fluid composition into progressively greater numbers of pathways.

3. The method of claim 1, wherein directing at least the few of the groups of multiple objects or directing one or more of the objects of the few groups through the one or more branch points comprises combining a plurality of objects directed through each of two or more branch points prior to directing the combined objects through a subsequent branch point.

4. The method of claim 1, wherein directing at least the few of the groups of multiple objects or directing one or more of the objects of the few groups through the one or more branch points comprises directing a plurality of objects through a branch point prior to directing at least one object of the plurality of objects through a subsequent branch point.

5. The method of claim 1, wherein analyzing the groups of multiple objects or the objects of the few groups comprises performing at least one of morphology measurements, luminescence measurements, fluorescence measurements, radioactive measurements, light scattering measurements, electrical measurements, or ultrasound measurements for use in determining one or more characteristics of the objects being analyzed.

6. The method of claim 1, wherein analyzing the groups of multiple objects or the objects of the few groups comprises taking two or more different measurements from the objects being analyzed.

7. The method of claim 1, wherein analyzing the groups of multiple objects or the objects of the few groups comprises:
   providing electromagnetic energy to the objects being analyzed;
   detecting electromagnetic energy returned from the objects being analyzed resulting in a measurement signal; and
   providing one or more characteristics of the objects being analyzed based on the measurement signal.

8. The method of claim 1, wherein transporting the fluid composition comprises adjusting a flow rate of the transportation of the fluid composition through one or more pathways during analysis of the objects.

9. The method of claim 1, wherein the method further comprises stopping the transportation of the fluid composition through one or more of the plurality of pathways during the analysis of the objects.

10. The method of claim 1, wherein directing at least the few of the groups of multiple objects comprises applying a magnetic field to direct the fluid composition based on the analysis of the objects.

11. The method of claim 1, wherein directing at least the few of the groups of multiple objects comprises operating a flow switching structure associated with a branch point based on the analysis of the objects.

12. The method of claim 1, wherein the objects comprise biological objects.

13. The method of claim 1, wherein the objects comprise non-biological objects.

14. The method of claim 13, wherein the non-biological object comprise particles.

15. The method of claim 1, wherein transporting the fluid composition comprises transporting the fluid composition through a plurality of pathways in a fluid tight system.

16. The method of claim 1, wherein the method further comprises providing makeup fluid into one or more of the plurality of pathways to increase the distance between multiple objects of the few groups.

17. method of claim 16, wherein the method further comprises changing at least one of a proportion of the makeup fluid and the fluid composition through one or more of the plurality of pathways during the analysis of the objects.

18. The method of claim 1, wherein at least one of one or more branch points is used to provide parallel pathways from a single combined pathway, wherein the single combined pathway is provided by pathways from a plurality of branch points.

19. The method of claim 1, wherein directing at least the few of the groups of multiple objects comprises sorting objects in a pathway by directing the objects through the at least one of the one or more branch points to one or more pathways having smaller cross sections such that the distance between multiple objects of the few groups is increased.

20. The method of claim 1, wherein at least one of the one or more branch points are used to provide parallel pathways from a single pathway, wherein the single pathway is provided by a pathway from a single branch point, wherein directing at least the few of the groups of multiple objects or directing one or more of the objects of the few groups comprises sorting objects in the single pathway by directing the objects through the at least one of the one or more branch points to one or more of the parallel pathways.

21. The method of claim 1, wherein the method further comprises performing single object analysis on a plurality of sorted objects, wherein the plurality of sorted objects are a result of directing objects in the plurality of pathways based on group analysis of multiple objects.

22. The method of claim 1, wherein the pathway network comprising one or more branch points forms a series of pathways, and wherein the method comprises repeatedly analyzing objects and directing one or more of the objects through multiple branch points based on the analysis of the objects to increase the percentage of objects of interest in the series of pathways relative to other objects present therein.

23. The method of claim 22, wherein analysis of the objects uses prior analysis of the objects in directing one or more of the objects through subsequent branch points.

24. The method of claim 1, wherein the pathway network comprising one or more branch points forms at least a portion of one or more sorting stages, wherein each sorting stage comprises at least one sorting module associated with each of a plurality of branch points.

25. The method of claim 24, wherein analyzing the groups of multiple objects or the objects of the few groups comprises analyzing objects during a particular period of time using each of the sorting modules of at least one sorting stage for use in directing the objects through associated branch points.

26. The method of claim 25, wherein analyzing the objects comprises analyzing objects at multiple sorting stages.

27. A sorting method, comprising:
   providing a pathway network comprising a plurality of pathways and one or more branch points;
   analyzing groups of cells suspended in a fluid composition at one or more positions along a pathway of the pathway network to detect cells of interest, wherein analyzing each group of cells comprises analyzing simultaneously the cells of the group together by providing a measurement taken on the cells of the group together, the measurement for use in determining a pathway of the pathway network down which the group is to be directed; and
   sorting the groups of cells, wherein sorting the groups of cells comprises directing at least a few of the groups of cells through one branch point of the one or more branch points down at least one pathway of the plurality of pathways based on the analysis of the groups of cells such that a distance between cells of the few groups is increased and directing other groups of cells down a pathway different than the at least one pathway to increase the percentage of cells of interest in the at least one pathway relative to other cells present therein, wherein the method further comprises analyzing cells of the few groups directed down the at least one pathway with increased distance between cells thereof to detect cells of interest, wherein analyzing the cells of the few groups comprises analyzing simultaneously multiple cells of the few groups together in a pathway by providing a measurement taken on the multiple cells of the few groups together in the pathway, the measurement for use in determining a pathway of the pathway network down which one or more of cells of the few groups is to be directed, and directing one or more of the cells of the few groups through another of the one or more branch points down another pathway of the pathway network based on the analysis of the cells of the few groups to further increase the percentage of cells of interest therein relative to other cells present therein.

28. The method of claim 27, wherein the plurality of pathways and the one or more branch points provide for a progressively greater number of pathways.

29. The method of claim 27, wherein directing at least the few groups of cells or directing one or more of the cells of the few groups comprises combining a plurality of cells directed through each of two or more branch points prior to directing the combined cells through a subsequent branch point.

30. The method of claim 27, wherein directing at least the few groups of cells or directing one or more of the cells of the few groups comprises directing a plurality of cells through a branch point prior to directing at least one cell of the plurality of cells through a subsequent branch point.

31. The method of claim 27, wherein analyzing the groups of cells or the cells of the few groups comprises performing at least one of morphology measurements, luminescence measurements, fluorescence measurements, radioactive measurements, light scattering measurements, electrical measurements, or ultrasound measurements for use in determining one or more characteristics of the cells being analyzed.

32. The method of claim 27, wherein analyzing the groups of cells or the cells of the few groups suspended in the fluid composition comprises taking two or more different measurements from the cells being analyzed.

33. The method of claim 27, wherein analyzing the groups of cells or the cells of the few groups suspended in the fluid composition comprises:
provided electromagnetic energy to the cells being analyzed;
detecting electromagnetic energy returned from the cells being analyzed resulting in a measurement signal; and
providing one or more characteristics of the cells being analyzed based on the measurement signal.

34. The method of claim 27, wherein the method further comprises transporting the fluid composition through one or more pathways.

35. The method of claim 34, wherein transporting the fluid composition further comprises adjusting a flow rate of at least a portion of the fluid composition through one or more pathways during analysis of the cells.

36. The method of claim 34, wherein the method further comprises stopping the transportation of the fluid composition through one or more of the plurality of pathways during the analysis of the cells.

37. The method of claim 34, wherein transporting the fluid composition comprises transporting the fluid composition through a plurality of pathways in a fluid tight system.

38. The method of claim 27, wherein directing at least the few groups of cells or directing one or more of the cells of the few groups comprises applying a magnetic field to sort the fluid composition based on the analysis of the cells.

39. The method of claim 27, wherein directing at least the few groups of cells or directing one or more of the cells of the few groups comprises operating a flow switching structure associated with a branch point based on the analysis of the cells.

40. The method of claim 27, wherein the method further comprises providing makeup fluid into one or more of the plurality of pathways to increase the distance between cells of the few groups.

41. The method of claim 27, wherein at least one of one or more branch points is used to provide parallel pathways from a single combined pathway, wherein the single combined pathway is provided by pathways from a plurality of branch points, and further wherein directing at least the few groups of cells or directing one or more of the cells of the few groups comprises sorting cells in the single combined pathway by directing one or more cells through the at least one of the one or more branch points to one or more of the parallel pathways.

42. The method of claim 27, wherein directing at least the few groups of cells or directing one or more of the cells of the few groups comprises sorting the cells in a pathway by directing one or more cells through the at least one of the one or more branch points to one or more pathways having a smaller cross sections such that the distance between multiple cells of the few groups is increased.

43. The method of claim 27, wherein the pathway network comprising one or more branch points forms a series of pathways, and further wherein the method comprises repeatedly analyzing cells and directing one or more of the cells through multiple branch points based on the analysis of the cells to increase the percentage of cells of interest in the series of pathways relative to other cells present therein.

44. The method of claim 27, wherein the pathway network comprising one or more branch points forms at least a portion of one or more sorting stages, wherein each sorting stage comprises at least one sorting module associated with each of a plurality of branch points.

45. The method of claim 44, wherein analyzing the groups of cells or the cells of the few groups comprises analyzing cells during a particular period of time using each of the sorting modules of at least one sorting stage for use in directing the cells through associated branch points.

46. The method of claim 45, wherein analyzing the cells comprises analyzing cells at multiple sorting stages.

47. The method of claim 27, wherein the method comprises performing single cell analysis on a plurality of sorted cells, wherein the plurality of sorted cells are a result of directing cells in the plurality of pathways based on group analysis of the cells.

* * * * *

UNITED STATES PATENT AND TRADEMARK OFFICE
CERTIFICATE OF CORRECTION

Page 1 of 1

PATENT NO. : 7,452,725 B2
APPLICATION NO. : 10/340520
DATED : November 18, 2008
INVENTOR(S) : Leary et al.

It is certified that error appears in the above-identified patent and that said Letters Patent is hereby corrected as shown below:

In the Specification

COLUMN 1, LINE 7; Prior to the TECHNICAL FIELD, insert the following:

--GOVERNMENT FUNDING
This invention was made with government support under R01-GM38645 awarded by the National Institutes of Health. The government has certain rights in the invention.--

Signed and Sealed this
First Day of September, 2015

Michelle K. Lee
*Director of the United States Patent and Trademark Office*